(12) United States Patent
Ogata et al.

(10) Patent No.: US 7,700,259 B2
(45) Date of Patent: Apr. 20, 2010

(54) POLYMER COMPOUND, PHOTORESIST COMPOSITION CONTAINING SUCH POLYMER COMPOUND, AND METHOD FOR FORMING RESIST PATTERN

(75) Inventors: Toshiyuki Ogata, Kawasaki (JP); Syogo Matsumaru, Kawasaki (JP); Hideo Hada, Kawasaki (JP); Masaaki Yoshida, Kawasaki (JP)

(73) Assignee: Tokyo Ohka Kogyo Co., Ltd., Kawasaki-shi (JP)

(*) Notice: Subject to any disclaimer, the term of this patent is extended or adjusted under 35 U.S.C. 154(b) by 441 days.

(21) Appl. No.: 11/578,189

(22) PCT Filed: Apr. 5, 2005

(86) PCT No.: PCT/JP2005/006657

§ 371 (c)(1),
(2), (4) Date: Oct. 11, 2006

(87) PCT Pub. No.: WO2005/100412

PCT Pub. Date: Oct. 27, 2005

(65) Prior Publication Data

US 2007/0224520 A1    Sep. 27, 2007

(30) Foreign Application Priority Data

Apr. 13, 2004  (JP) ............ P2004-117693
Jun. 18, 2004  (JP) ............ P2004-181067
Jun. 18, 2004  (JP) ............ P2004-181068

(51) Int. Cl.
  G03C 1/00   (2006.01)
  C07C 69/74  (2006.01)
(52) U.S. Cl. .............. 430/270.1; 560/1; 560/127
(58) Field of Classification Search ............. 430/270.1, 430/288.1, 285.1, 286.1; 560/1, 127
See application file for complete search history.

(56) References Cited

U.S. PATENT DOCUMENTS

| | | | |
|---|---|---|---|
| 1,985,343 A | | 12/1934 | Connolly et al. |
| 4,269,933 A | * | 5/1981 | Pazos .................... 430/291 |
| 4,530,747 A | | 7/1985 | Dönges et al. |
| 5,216,135 A | | 6/1993 | Urano et al. |
| 5,849,808 A | | 12/1998 | Schracht et al. |
| 5,942,367 A | | 8/1999 | Watanabe et al. |
| 5,994,022 A | * | 11/1999 | Tanabe et al. ............. 430/170 |
| 6,114,462 A | | 9/2000 | Watanabe et al. |
| 6,632,586 B1 | * | 10/2003 | Aoai et al. ............... 430/287.1 |
| 2001/0003640 A1 | | 6/2001 | Takechi et al. |
| 2002/0034704 A1 | | 3/2002 | Oomori et al. |
| 2002/0051938 A1 | * | 5/2002 | Trefonas et al. .......... 430/270.1 |
| 2002/0068238 A1 | | 6/2002 | Hada et al. |

FOREIGN PATENT DOCUMENTS

| | | |
|---|---|---|
| EP | 0738744 A2 | 10/1996 |
| EP | 1262830 A1 | 12/2002 |
| JP | 04-039665 | 2/1992 |
| JP | 10-031310 | 2/1998 |
| JP | 2001-318465 | 11/2001 |
| JP | 2002296782 A * | 10/2002 |
| JP | 2003-233177 | 8/2003 |
| WO | WO 94/17057 | 8/1994 |

OTHER PUBLICATIONS

Hagiwara et al. *Journal of Photopolymer Science and Technology.* 16(4):557-564 (2003).
Houlihan et al. *Journal of Photopolymer Science and Technology.* 16(4):581-590 (2003).
Kawaguchi et al. *Proceedings of SPIE.* 5039:43-52 (2003).
Supplementary Search Report for Application No. EP 05728789.8 dated Feb. 3, 2010.

* cited by examiner

Primary Examiner—Cynthia H Kelly
Assistant Examiner—Connie P Johnson
(74) Attorney, Agent, or Firm—Knobbe, Martens, Olson & Bear, LLP

(57) ABSTRACT

A polymer compound that, within a chemically amplified positive resist system, exhibits a significant change in alkali solubility from a state prior to exposure to that following exposure, as well as a photoresist composition that includes such a polymer compound and a method for forming a resist pattern, which are capable of forming fine patterns with a high level of resolution. The polymer compound includes, as an alkali-soluble group (i), a substituent group in which a group selected from amongst alcoholic hydroxyl groups, carboxyl groups, and phenolic hydroxyl groups is protected with an acid dissociable, dissolution inhibiting group (ii) represented by a general formula (1) shown below:

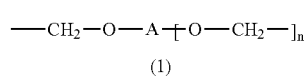

[Formula 1]

(1)

(wherein, A represents an organic group of 1 to 20 carbon atoms with a valency of at least n+1, and n represents an integer from 1 to 4).

14 Claims, No Drawings

POLYMER COMPOUND, PHOTORESIST COMPOSITION CONTAINING SUCH POLYMER COMPOUND, AND METHOD FOR FORMING RESIST PATTERN

CROSS-REFERENCE TO RELATED APPLICATIONS

This application is the U.S. National Phase filing under 35 U.S.C. §371 of PCT/JP2005/006657, filed Apr. 5, 2005, which designated the United States and was published in a language other than English, which claims priority under 35 U.S.C. §119(a)-(d) to Japanese Patent Application Nos. 2004-117693, filed Apr. 13, 2004; 2004-181067, filed Jun. 18, 2004; and 2004-181068, filed Jun. 18, 2004. The content of these applications is incorporated herein by reference in their entireties.

TECHNICAL FIELD

The present invention relates to a polymer compound used in the patterning of a semiconductor integrated circuit by lithography, as well as a photoresist composition containing such a polymer compound, and a method for forming a resist pattern, and relates more specifically to a polymer compound for a photoresist composition that exhibits superior resolution characteristics upon fine patterning using a light source with a wavelength of no more than 300 nm, and particularly a KrF, ArF or $F_2$ excimer laser, as well as a photoresist composition containing such a polymer compound, and a method for forming a resist pattern.

BACKGROUND ART

It is not an exaggeration to say that the miniaturization of semiconductor integrated circuits has been achieved as a result of developments in photolithography and associated technologies. As is widely known, these photolithography developments are supported by what can be broadly classified as two technologies. One is the exposure wavelength and numerical aperture of the reduction projection exposure apparatus known as a stepper or scanner, and the other is the resist characteristics, and mainly the transferred resolution of a photoresist composition generated by transferring a mask pattern using the above reduction projection exposure apparatus. A combination of these technologies has brought significant improvements in the precision of the processing of semiconductor integrated circuit patterns by photolithography.

The light source used in the reduction projection exposure apparatus has continued to shift towards shorter wavelengths in order to meet the demands for higher resolution circuit patterns. Typically, for a resist resolution of 0.5 µm, a mercury lamp for which the main spectrum is the 436 nm g-line is used, for a resolution of approximately 0.5 to 0.30 µm, a mercury lamp for which the main spectrum is the 365 nm i-line is used, for a resolution of approximately 0.3 to 0.15 µm, 248 nm KrF excimer laser light is used, and for resolutions of 0.15 µm or less, 193 nm ArF excimer laser light is used, and in order to achieve even greater miniaturization, 157 nm $F_2$ excimer laser light, 126 nm $Ar_2$ excimer laser light and EUV (extreme ultraviolet radiation: wavelength 13 nm) are also being investigated.

On the other hand, in the case of photoresist compositions, combinations with organic and inorganic antireflective films and innovations within the illumination systems are now commonplace, and in the case of lithography using KrF excimer laser light, photoresist compositions that will enable prolonged life for KrF photoresists are being developed, including photoresist compositions that target resolutions of approximately 110 nm, which represents no more than λ/2. Furthermore, in the case of lithography using ArF excimer lasers, favorable ArF photoresist compositions that will enable future mass production of fine patterns with a 90 nm node or smaller are now being sought. Moreover, lithography using the aforementioned $F_2$ excimer lasers is now attracting considerable attention as a technology that will take a pivotal role in the processing of future ultra fine patterns of 65 nm or smaller, and considerable development is now being pursued of photoresist compositions that can be favorably applied to microfabrication using such $F_2$ excimer laser lithography.

Obtaining the types of fine patterns described above using conventional positive photoresist compositions that include an alkali-soluble novolak resin and a quinonediazide group-containing compound as the main components is extremely difficult, and the development of resists that use shorter wavelength radiation, including far ultraviolet light (200 to 300 nm), excimer lasers such as KrF or ArF lasers, electron beams or X-rays, is now keenly sought. One type of resist that is attracting considerable attention as a resist capable of achieving high levels of resolution, capable of utilizing a catalytic reaction and chain reaction caused by acid generated upon irradiation to produce a quantum yield of 1 or greater, and also capable of achieving high sensitivity is a chemically amplified resist, and development of these resists is flourishing.

Resists for use with short wavelength light sources such as KrF excimer lasers or ArF excimer lasers require a high level of resolution capable of reproducing a pattern of very fine dimensions, as well as high sensitivity to this type of short wavelength light source. One example of a known resist capable of satisfying these requirements is a chemically amplified positive resist composition which includes a base resin that exhibits increased alkali solubility under the action of acid, and an acid generator that generates acid on exposure.

Chemically amplified positive resist compositions that have been proposed as ideal resist materials for exposure methods using a KrF excimer laser typically employ a polyhydroxystyrene-based resin in which a portion of the hydroxyl groups have been protected with acid dissociable, dissolution inhibiting groups as the base resin (for example, see patent reference 1). Examples of the most commonly used acid dissociable, dissolution inhibiting groups include so-called acetal groups, such as chain-like ether groups typified by a 1-ethoxyethyl group and cyclic ether groups typified by a tetrahydropyranyl group, as well as tertiary alkyl groups such as a tert-butyl group or 2-alkyl-2-adamantyl group, and tertiary alkoxycarbonyl groups typified by a tert-butoxycarbonyl group.

Furthermore, chemically amplified positive resist compositions that have been proposed as ideal resist materials for exposure methods using an ArF excimer laser typically employ, as the base resin, a (meth)acrylate-based resin in which a portion of the hydroxyl groups have been protected with the same type of acid dissociable, dissolution inhibiting groups as those described above. Of these, resins that use a tertiary alkyl group as the acid dissociable, dissolution inhibiting group are particularly widely used (for example, see patent reference 2).

As disclosed in the non-patent references (3 to 5) listed below, examples of the above chemically amplified resists include fluoroalcohols containing an acetal group, a tertiary alkyl group such as a tert-butyl group, a tert-butoxycarbonyl group or a tert-butoxycarbonylmethyl group as the acid dissociable, dissolution inhibiting group.

[Patent Reference 1]
Japanese Unexamined Patent Application, First Publication No. Hei 04-211258
[Patent Reference 2]
Japanese Patent (Granted) Publication No. 2,881,969
[Non-Patent Reference 3]
T. Hagiwara, S. Irie, T. Itani, Y. Kawaguchi, O. Yokokoji, and S. Kodama, J. Photopolym. Sci. Technol., Vol. 16, p. 557, 2003
[Non-Patent Reference 4]
F. Houlihan, A. Romano, D. Rentkiewicz, R. Sakamuri, R. R. Dammel, W. Conley, G. Rich, D. Miller, L. Rhodes, J. McDaniels and C. Chang, J. Photopolym. Sci. Technol., Vol. 16, p. 581, 2003
[Non-Patent Reference 5]
Y. Kawaguchi, J. Irie, S. Kodama, S. Okada, Y. Takabe, I. Kaneko, O. Yokokoji, S. Ishikawa, S. Irie, T. Hagiwara and T. Itani, Proc. SPIE, Vol. 5039, p. 43, 2003.

DISCLOSURE OF INVENTION

Problems to be Solved by the Invention

In recent years, the miniaturization of resist patterns has continued to progress, and further improvements in both resolution and sensitivity are keenly sought.

However, there is a limit to the improvement in resolution achievable using conventional chemically amplified resists such as those disclosed in the above patent references 1 and 2.

Furthermore, the fact that the types of acid generator that can be used are restricted is another problem. Namely, if an acid generator is used for which the strength of the acid generated is weak, then there is a danger that the acid dissociable, dissolution inhibiting groups such as the tertiary alkyl groups may not undergo adequate dissociation, meaning satisfactory resolution of the resist pattern becomes impossible. As a result, onium salts that contain a fluorinated alkylsulfonate ion as the anion portion, which generate strong acids, are currently the most widely used acid generators.

The present invention takes the above circumstances into consideration, with an object of providing a polymer compound capable of forming a positive resist composition that exhibits excellent resolution, and is capable of favorably resolving a resist pattern even if an acid generator that generates only a weak acid is used, as well as providing ideal compounds for producing the polymer compound, a positive resist composition that includes the polymer compound, and a method for forming a resist pattern that uses the positive resist composition.

Furthermore, the chemically amplified resists disclosed in the above non-patent references 3 through 5 do not provide completely satisfactory levels of resist pattern resolution and shape, and further improvements are still desirable.

The present invention takes these circumstances into consideration, with an object of providing a polymer compound with a novel acid dissociable, dissolution inhibiting group that yields excellent resist pattern resolution and pattern shape, as well as a photoresist composition that includes the polymer compound, and a method for forming a resist pattern.

Means for Solving the Problems

In order to achieve the objects described above, the inventors of the present invention tested all manner of acid dissociable, dissolution inhibiting groups as potential protective groups for the alkali-soluble groups of polymer compounds used in photoresist compositions, and based on intensive research of the resist characteristics of the resulting polymer compounds, discovered that by using a polyfunctional acid dissociable, dissolution inhibiting group represented by a specific general formula, a fine resist pattern with improved pattern resolution could be formed, and based on this finding, they were able to complete the present invention.

The present invention is based on the above finding. In other words, a first aspect of the present invention provides a polymer compound that exhibits changed alkali solubility under the action of acid, wherein the polymer compound includes an alkali-soluble group (i) that contains a hydroxyl group, and the hydrogen atom of this hydroxyl group is protected with an acid dissociable, dissolution inhibiting group (ii) represented by a general formula (1) shown below.

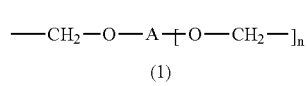

[Formula 1]

(1)

(wherein, A represents an organic group of 1 to 20 carbon atoms with a valency of at least n+1, and n represents an integer from 1 to 4)

The alkali-soluble group (i) is preferably an alcoholic hydroxyl group, a phenolic hydroxyl group, or a carboxyl group. Alcoholic hydroxyl groups in which the carbon atom adjacent to the carbon atom bearing the alcoholic hydroxyl group is bonded to at least one fluorine atom are particularly desirable.

In the above general formula (1), A is preferably a hydrocarbon group with a chain-like or cyclic structure that contains from 1 to 20 carbon atoms and has a valency of at least n+1.

A second aspect of the present invention represents one particular variety of the polymer compound according to the first aspect described above, which includes a structural unit (a1) represented by a general formula (51) shown below.

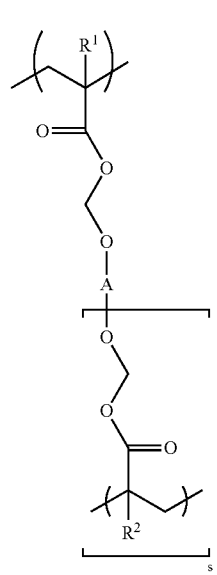

[Formula 2]

(51)

[wherein, $R^1$ and $R^2$ each represent, independently, a hydrogen atom or a methyl group; s represents an integer from 1 to 4; and A represents an organic group of 1 to 20 carbon atoms with a valency of (s+1)]

A third aspect of the present invention is a compound that can act as the synthetic raw material for the polymer compound according to the second aspect described above, wherein the compound is represented by a general formula (41) shown below.

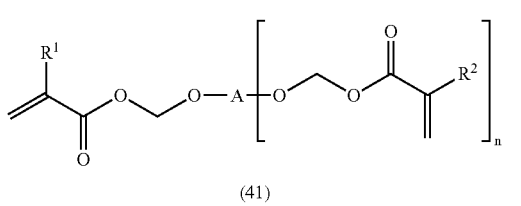

[Formula 3]

(41)

[wherein, $R^1$ and $R^2$ each represent, independently, a hydrogen atom or a methyl group; n represents an integer from 1 to 4, and A represents a hydrocarbon group of 1 to 20 carbon atoms with a valency of (n+1)]

A fourth aspect of the present invention is a positive resist composition that includes a polymer compound (A) according to either of the first and second aspects described above, and an acid generator component (B) that generates acid on exposure.

A fifth aspect of the present invention is a method for forming a resist pattern that includes the steps of applying the positive resist composition according to the aforementioned fourth aspect to a substrate, conducting a prebake, performing selective exposure, conducting PEB (post exposure baking), and performing alkali developing to form the resist pattern.

In the present invention, the term "structural unit" refers to a monomer unit that contributes to the formation of a polymer compound.

Furthermore, the term "exposure" is used as a general concept that includes irradiation with any form of radiation.

EFFECTS OF THE INVENTION

The present invention enables the provision of a polymer compound capable of forming a positive resist composition that exhibits excellent resolution and is capable of favorably resolving a resist pattern even if an acid generator that generates only a weak acid is used, and also provides ideal compounds for producing the polymer compound, a positive resist composition that includes the polymer compound, and a method for forming a resist pattern that uses the positive resist composition. Furthermore, the present invention also enables the prevention of thickness loss of the resist pattern.

BEST MODE FOR CARRYING OUT THE INVENTION

As follows is a description of embodiments of the present invention.

In a polymer compound according to the first aspect of the present invention, the hydrogen atoms of the hydroxyl groups of the alkali-soluble groups (i) within the polymer compound molecules are protected with acid dissociable, dissolution inhibiting groups (ii) represented by a general formula (1) shown below.

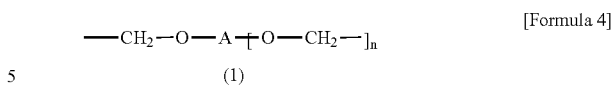

[Formula 4]

(1)

(wherein, A represents an organic group of 1 to 20 carbon atoms with a valency of at least n+1, and n represents an integer from 1 to 4)

If a polymer compound of the present invention is used within a chemically amplified positive resist system, then because the polymer compound includes the polyfunctional acid dissociable, dissolution inhibiting groups represented by the above general formula (1), the compound exhibits a powerful alkali solubility inhibiting effect prior to exposure, but following exposure and PEB, the compound develops alkali solubility as a result of the deprotection of the acid dissociable, dissolution inhibiting groups, meaning the alkali solubility changes significantly from the state prior to exposure to that following exposure, thereby enabling a fine pattern with a high level of resolution to be achieved. Furthermore, thickness loss of the resist pattern can also be prevented.

This alkali-soluble group (i) is preferably an alcoholic hydroxyl group, a phenolic hydroxyl group, or a carboxyl group, and alcoholic hydroxyl groups in which the carbon atom adjacent to the carbon atom bearing the alcoholic hydroxyl group is bonded to at least one fluorine atom are particularly desirable.

In the above general formula, A is preferably a hydrocarbon group with a chain-like or cyclic structure that contains from 1 to 20 carbon atoms and has a valency of at least n+1.

In this description, the term "polyfunctional" describes a state wherein, as shown in the general formula (1), the organic group A, which has multiple bond linkages and contains —O—$CH_2$— groupings bonded to at least a portion of those bond linkages, is able to bond to a plurality of alkali-soluble groups (i).

The acid dissociable, dissolution inhibiting group (ii) is represented by the general formula (1) shown above, and in this formula, A represents an organic group of 1 to 20 carbon atoms with a valency of at least n, so that when n=1, A is a bivalent or higher organic group, and two bond linkages of the two or more bond linkages emanating from A are bonded to —O—$CH_2$— groups. In general, if the number of —O—$CH_2$— groups is n+1, A is an organic group with a valency of at least n+1, and of the n+1 or greater bond linkages emanating from A, n+1 bond linkages are bonded to —O—$CH_2$— groups. Of the various possibilities, organic groups with a valency of n+1 are preferred. In such cases, all of the bond linkages emanating from A are bonded to —O—$CH_2$— groups, and the acid dissociable, dissolution inhibiting group (ii) for the cases where n+1 represents a bivalent group through to a pentavalent group can be represented by the following general formulas (2) through (5) respectively.

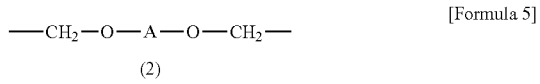

[Formula 5]

(2)

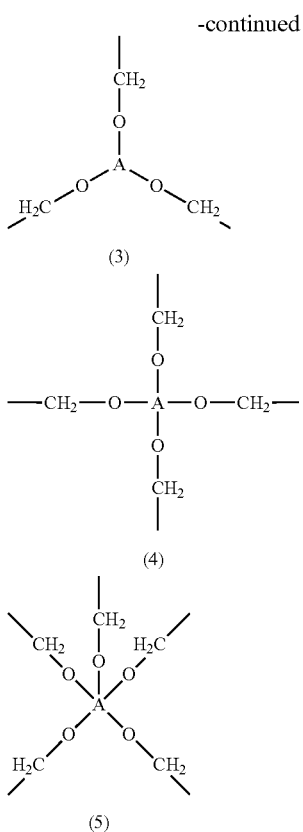

(3)

(4)

(5)

The acid dissociable, dissolution inhibiting group (ii) is bonded to the aforementioned polymer compound that includes one type of alkali-soluble group (i) selected from the group consisting of alcoholic hydroxyl groups, phenolic hydroxyl groups and carboxyl groups, and is bonded to the oxygen atom of the alkali-soluble group (i) from which the hydrogen atom has been removed. The alkali-soluble groups (i) bonded to the acid dissociable, dissolution inhibiting group (ii) may either be groups within the same molecule of the polymer compound, or may be groups from different molecules of the polymer compound. Of these possibilities, the case in which the alkali-soluble groups (i) exist within the same molecule of the polymer compound is preferred.

In the aforementioned acid dissociable, dissolution inhibiting group (ii), A represents an organic group, and suitable examples include a chain-like, branched, or cyclic saturated aliphatic or unsaturated aliphatic hydrocarbon group of 1 to 20 carbon atoms. Of such groups, chain-like, branched, or cyclic saturated aliphatic or unsaturated aliphatic hydrocarbon group of 1 to 16, and preferably 1 to 12, carbon atoms are more readily produced industrially, and are consequently preferred.

Examples of the above chain-like or branched hydrocarbon groups include groups in which one or more hydrogen atoms have been removed from a methyl group, ethyl group, n-propyl group, isopropyl group, n-butyl group, isobutyl group, n-pentyl group, cyclopentyl group, methylcyclopentyl group, ethylcyclopentyl group, n-hexyl group, cyclohexyl group, methylcyclohexyl group, ethylcyclohexyl group, heptyl group, octyl group, nonyl group, decanyl group or dodecanyl group or the like. Of these, alkylene groups of 1 to 5 carbon atoms are preferred, and a methylene group or n-propylene group is the most desirable.

Examples of the above cyclic hydrocarbon group include groups in which two or more hydrogen atoms have been removed from a cycloalkane, bicycloalkane, bicycloalkene, tricycloalkane, tetracycloalkane, methylbicycloalkane, methylbicycloalkene, methyltricycloalkane, methyltetracycloalkane, ethylbicycloalkane, ethylbicycloalkene, ethyltricycloalkane, or ethyltetracycloalkane or the like.

Specific examples include groups in which two or more hydrogen atoms have been removed from cyclohexane, cyclopentane, or a polycycloalkane such as adamantane, norbornane, norbornene, methylnorbornane, ethylnorbornane, methylnorbornene, ethylnorbornene, isobornane, tricyclodecane or tetracyclododecane. These types of polycyclic groups can be selected appropriately from the multitude of groups proposed for use with ArF resists. Of the various possibilities, cycloalkyl groups are preferred, and groups in which two hydrogen atoms have been removed from cyclohexane are the most desirable.

The alkali-soluble sites (i) in a polymer compound of the present invention are already well known, from the aforementioned non-patent references, or from the KrF resists, ArF resists and $F_2$ resists that have previously been proposed. There are no particular restrictions on these alkali-soluble sites, and suitable examples include alcoholic hydroxyl groups, phenolic hydroxyl groups, carboxyl groups and the like.

In the present invention, these alkali-soluble sites preferably include one or more groups selected from the group consisting of alcoholic hydroxyl groups, phenolic hydroxyl groups and carboxyl groups. Of these, alcoholic hydroxyl groups or fluorine-containing alcoholic hydroxyl groups exhibit excellent transparency and also yield a suitable level of alkali solubility, and are consequently ideal.

The alcoholic hydroxyl group may be simply a hydroxyl group, or may also be an alkyloxy group, alkyloxyalkyl group or alkyl group that contains a hydroxyl group, namely an alcoholic hydroxyl group-containing alkyloxy group, alcoholic hydroxyl group-containing alkyloxyalkyl group, or alcoholic hydroxyl group-containing alkyl group. Examples of the alkyloxy group, alkyloxyalkyl group or alkyl group include lower alkyloxy groups, lower alkyloxy-lower alkyl groups, and lower alkyl groups respectively. In this description, the number of carbon atoms within a group represented by the term "lower" is preferably from 1 to 5.

Specific examples of the above lower alkyloxy groups include a methyloxy group, ethyloxy group, propyloxy group and butyloxy group, specific examples of the lower alkyloxy-lower alkyl groups include a methyloxymethyl group, ethyloxymethyl group, propyloxymethyl group and butyloxymethyl group, and specific examples of the lower alkyl groups include a methyl group, ethyl group, propyl group and butyl group.

Furthermore, in the aforementioned alcoholic hydroxyl group-containing alkyloxy group, alcoholic hydroxyl group-containing alkyloxyalkyl group, or alcoholic hydroxyl group-containing alkyl group, either a portion of, or all of, the hydrogen atoms of the alkyloxy group, alkyloxyalkyl group or alkyl group may be substituted with fluorine atoms. Preferred groups include groups in which a portion of the hydrogen atoms within the alkyloxy section of an alcoholic hydroxyl group-containing alkyloxy group or alcoholic hydroxyl group-containing alkyloxyalkyl group have been substituted with fluorine atoms, and groups in which a portion of the hydrogen atoms within the alkyl group of an alcoholic hydroxyl group-containing alkyl group have been substituted with fluorine atoms, that is, alcoholic hydroxyl group-containing fluoroalkyloxy groups, alcoholic hydroxyl group-containing fluoroalkyloxyalkyl groups, and alcoholic hydroxyl group-containing fluoroalkyl groups.

Examples of the above alcoholic hydroxyl group-containing fluoroalkyloxy groups include a (HO)C(CF$_3$)$_2$CH$_2$O— group, 2-bis(trifluoromethyl)-2-hydroxy-ethyloxy group, (HO)C(CF$_3$)$_2$CH$_2$CH$_2$O— group and 3-bis(trifluoromethyl)-3-hydroxypropyloxy group, examples of the above alcoholic hydroxyl group-containing fluoroalkyloxyalkyl groups include a (HO)C(CF$_3$)$_2$CH$_2$O—CH$_2$— group and a (HO)C(CF$_3$)$_2$CH$_2$CH$_2$O—CH$_2$— group, and examples of the above alcoholic hydroxyl group-containing fluoroalkyl groups include a (HO)C(CF$_3$)$_2$CH$_2$— group, 2-bis(trifluoromethyl)-2-hydroxyethyl group, (HO)C(CF$_3$)$_2$CH$_2$CH$_2$— group and 3-bis(trifluoromethyl)-3-hydroxypropyl group.

Because they can be obtained relatively easily and cheaply, suitable examples of the aforementioned phenolic hydroxyl groups include the phenolic hydroxyl groups contained within novolak resins and polyhydroxystyrenes and the like. Of these, the phenolic hydroxyl groups of polyhydroxystyrenes are preferred as they provide excellent resolution that is ideal for fine patterns.

Examples of the aforementioned carboxyl groups include the carboxyl groups within ethylenic unsaturated carboxylic acids. Specific examples of such ethylenic unsaturated carboxylic acids include unsaturated carboxylic acids such as acrylic acid, methacrylic acid, maleic acid, and fumaric acid. Of these, acrylic acid and methacrylic acid are particularly preferred as they can be obtained relatively easily and cheaply.

Although there are no particular restrictions on the polystyrene equivalent weight average molecular weight of the polymer compound of the present invention, as determined by gel permeation chromatography (GPC), a value within a range from 5,000 to 150,000 is preferred, and a value from 40,000 to 130,000 is even more desirable. Furthermore, the polydispersity (Mw/Mn) is typically within a range from approximately 1.0 to 5.0, and is preferably no higher than 2.5.

The polymer compound of the present invention can be formed from at least one, or alternatively two or more, units selected from amongst monomer units that contain an aforementioned alcoholic hydroxyl group, phenolic hydroxyl group or carboxyl group, and the polymer compound may also include units used within the polymer compounds of conventional photoresist compositions, or may be mixed with such polymers.

Examples of polymer compounds containing alkali-soluble groups (i) that can act as precursors to the polymer compound of the present invention include polymer compounds represented by chemical formulas (6) through (14) shown below, which contain units derived from a compound containing an alcoholic hydroxyl group wherein the carbon atoms adjacent to the carbon atom to which the alcoholic hydroxyl group is bonded include at least one fluorine atom, as well as polymer compounds represented by a chemical formula (15), which contain units derived from a compound containing a phenolic hydroxyl group, such as a hydroxystyrene unit or α-methylhydroxystyrene unit, and compounds represented by a chemical formula (16), which contain a carboxyl group such as methacrylic acid or acrylic acid. Of these, the chemical formula (6) and the chemical formula (13) are readily available industrially, and are consequently preferred.

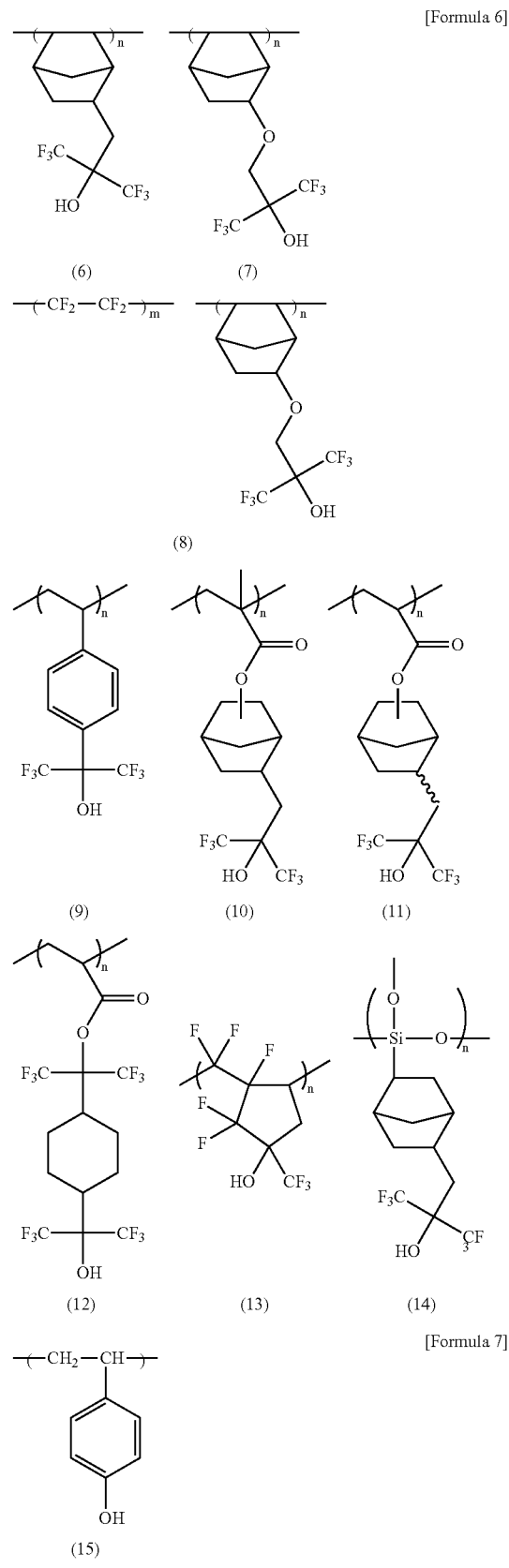

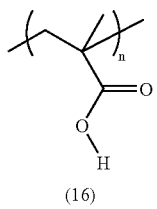

[Formula 8]

(16)

In a polymer compound of the present invention, from the viewpoints of resolution and thickness loss, from 5 to 50%, and preferably from 8 to 40% of the hydroxyl groups of the alkali-soluble groups (i) are preferably protected with the acid dissociable, dissolution inhibiting groups (ii).

When the acid dissociable, dissolution inhibiting group represented by the above general formula (1) within the polymer compound of the present invention is used to substitute the hydrogen atom of the hydroxyl group of the alkali-soluble group (i) of a conventional low molecular weight compound that contains at least one alkali-soluble group (i) selected from amongst alcoholic hydroxyl groups, phenolic hydroxyl groups, carboxyl groups and the like, the resulting structure can be used as a low molecular weight compound that functions as a dissolution inhibitor within a photoresist composition. These low molecular weight compounds are characterized by the alkali-soluble group (i) within the molecule being protected with the acid dissociable, dissolution inhibiting group (ii). If such a low molecular weight compound for a photoresist composition is used within a chemically amplified positive resist system as an acid dissociable, dissolution inhibitor (C), then the compound exhibits an inhibiting effect upon alkali developing prior to exposure, but then following the exposure and PEB processes, develops alkali solubility as a result of deprotection, meaning the alkali solubility changes significantly from the state prior to exposure to that following exposure, thereby enabling a fine pattern with a high level of resolution to be achieved. Furthermore, thickness loss of the resist pattern can also be prevented. Furthermore, as a result of the effect of the hydrophilic groups contained within the low molecular weight compound, the adhesion of the resist pattern to the substrate improves, and the affinity for the alkali developing solution also improves, enabling a reduction in the level of developing defects.

These alkali-soluble groups (i) are preferably alcoholic hydroxyl groups, phenolic hydroxyl groups or carboxyl groups, and alcoholic hydroxyl groups in which the carbon atom adjacent to the carbon atom bearing the alcoholic hydroxyl group includes at least one fluorine atom are particularly desirable.

In the above general formula, A is preferably a hydrocarbon group with a chain-like or cyclic structure that contains from 1 to 20 carbon atoms and has a valency of at least n.

As described above for the case within the polymer compound of the present invention, the acid dissociable, dissolution inhibiting group (ii) is represented by the general formula (1) shown above, and in this formula, A represents an alkyl group of 1 to 20 carbon atoms with a valency of at least n+1, and n represents an integer from 1 to 4. When n=1, A is a bivalent or higher organic group, and two bond linkages of the two or more bond linkages emanating from A are bonded to —O—CH$_2$— groups. In general, if the number of —O—CH$_2$— groups is n+1, A is an organic group with a valency of n+1, and of the n+1 or greater bond linkages emanating from A, n+1 bond linkages are bonded to —O—CH$_2$— groups. Of the various possibilities, organic groups with a valency of n+1 are preferred. In such cases, all of the bond linkages emanating from A are bonded to —O—CH$_2$— groups, and the acid dissociable, dissolution inhibiting group (ii) for the cases where n+1 represents a bivalent group through to a pentavalent group can be represented by the aforementioned general formulas (2) through (5) respectively.

The acid dissociable, dissolution inhibiting group (ii) is bonded to the aforementioned low molecular weight compound that contains one type of alkali-soluble group (i) selected from the group consisting of alcoholic hydroxyl groups, phenolic hydroxyl groups and carboxyl groups, and is bonded to the oxygen atom of the alkali-soluble group (i) from which the hydrogen atom has been removed. The alkali-soluble groups (i) bonded to the acid dissociable, dissolution inhibiting group (ii) may either be groups within the same molecule of the lower molecular weight compound, or may be groups from different molecules of the low molecular weight compound. Of these possibilities, the case in which the alkali-soluble groups (i) exist within the same molecule of the low molecular weight compound is preferred.

In the aforementioned acid dissociable, dissolution inhibiting group (ii), A represents an organic group, and suitable examples include a chain-like, branched, or cyclic saturated aliphatic or unsaturated aliphatic hydrocarbon group of 1 to 20 carbon atoms. Of such groups, chain-like, branched, or cyclic saturated aliphatic or unsaturated aliphatic hydrocarbon group of 1 to 16, and preferably 1 to 12, carbon atoms are more readily produced industrially, and are consequently preferred.

Examples of the above chain-like or branched hydrocarbon groups include groups in which one or more hydrogen atoms have been removed from a methyl group, ethyl group, n-propyl group, isopropyl group, n-butyl group, isobutyl group, n-pentyl group, cyclopentyl group, methylcyclopentyl group, ethylcyclopentyl group, n-hexyl group, cyclohexyl group, methylcyclohexyl group, ethylcyclohexyl group, heptyl group, octyl group, nonyl group, decanyl group or dodecanyl group or the like. Of these, alkylene groups of 1 to 5 carbon atoms are preferred, and a methylene group or n-propylene group is the most desirable.

Examples of the above cyclic hydrocarbon group include groups in which two or more hydrogen atoms have been removed from a cycloalkane, bicycloalkane, bicycloalkene, tricycloalkane, tetracycloalkane, methylbicycloalkane, methylbicycloalkene, methyltricycloalkane, methyltetracycloalkane, ethylbicycloalkane, ethylbicycloalkene, ethyltricycloalkane, or ethyltetracycloalkane or the like.

Specific examples include groups in which two or more hydrogen atoms have been removed from cyclohexane, cyclopentane, or a polycycloalkane such as adamantane, norbornane, norbornene, methylnorbornane, ethylnorbornane, methylnorbornene, ethylnorbornene, isobornane, tricyclodecane or tetracyclododecane. These types of polycyclic groups can be selected appropriately from the multitude of groups proposed for use with ArF resists. Of the various possibilities, cycloalkyl groups are preferred, and groups in which two hydrogen atoms have been removed from cyclohexane are the most desirable.

The alkali-soluble sites (i) in the aforementioned low molecular weight compound for a photoresist composition are already well known from the KrF resists, ArF resists and F$_2$ resists that have previously been proposed. There are no particular restrictions on the alkali-soluble sites, and suitable examples include alcoholic hydroxyl groups, phenolic hydroxyl groups, carboxyl groups and the like.

In the above low molecular weight compound for a photoresist composition, the alkali-soluble sites preferably include one or more hydroxyl groups selected from the group consisting of alcoholic hydroxyl groups, phenolic hydroxyl groups and carboxyl groups. Of these, alcoholic hydroxyl groups in which the carbon atom adjacent to the carbon atom bearing the alcoholic hydroxyl group includes at least one fluorine atom are particularly desirable.

Examples of the aforementioned low molecular weight compound for a photoresist composition include the compounds with alcoholic hydroxyl groups represented by the chemical formulas (17) and (18) below, wherein the carbon atoms adjacent to a carbon atom to which an alcoholic hydroxyl group is bonded include at least one fluorine atom, as well as the compounds containing phenolic hydroxyl groups described below, and the compounds containing carboxyl groups described below.

[Formula 9]

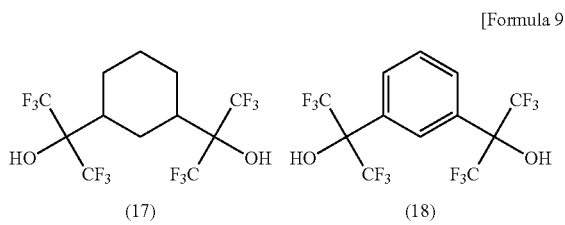

(17) (18)

As the aforementioned compounds containing phenolic hydroxyl groups, the types of polyhydric phenol compounds known as sensitizers or heat resistance improvement agents for non-chemically amplified g-line or i-line resists can be used. Specific examples of these polyhydric phenols include the compounds listed below:

bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, bis(4-hydroxy-3,5-dimethylphenyl)-2-hydroxyphenylmethane, bis(4-hydroxy-3,5-dimethylphenyl)-4-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(4-hydroxy-3-methylphenyl)-2-hydroxyphenylmethane, bis(3-cyclohexyl-4-hydroxy-6-methylphenyl)-2-hydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, bis(4-hydroxy-3,5-dimethylphenyl)-2-hydroxyphenylmethane, bis(4-hydroxy-2,3,5-trimethylphenyl)-2-hydroxyphenylmethane, bis(4-hydroxy-2,3,5-trimethylphenyl)-3-hydroxyphenylmethane, bis(4-hydroxy-2,3,5-trimethylphenyl)-4-hydroxyphenylmethane, 1-[1-(4-hydroxyphenyl)isopropyl]-4-[1,1-bis(4-hydroxyphenyl)ethyl]benzene, and four-benzene ring compounds of formalin condensation products of phenols such as phenol, m-cresol, p-cresol and xylenol.

Examples of the aforementioned compounds containing carboxyl groups include conventional bile acids such as cholic acid and litholithic acid, which are known as dissolution inhibitor precursors for chemically amplified resists.

A polymer compound or low molecular weight compound for a photoresist composition containing a specific acid dissociable, dissolution inhibiting group of the present invention can be synthesized by conventional methods, such as the methods disclosed in the aforementioned non-patent references.

A polymer compound or low molecular weight compound for a photoresist composition according to the present invention can be prepared using an alcohol compound as the starting material, synthesizing the chloromethyl ether of this alcohol as an acid dissociable, dissolution inhibiting group precursor, and having synthesized this precursor, reacting it with a low molecular weight compound or polymer compound that contains alkali-soluble groups to obtain the target compound.

For example, the target compound can be obtained using a chloromethyl ether compound as the starting raw material, and reacting this compound with a polymer compound or low molecular weight compound containing one type of substituent selected from amongst alcoholic hydroxyl groups, phenolic hydroxyl groups and carboxyl groups.

The above chloromethyl ether compound can be synthesized using a method represented by the reaction formula shown below. In other words, paraformaldehyde is added to the alcohol compound, and a reaction is then conducted at 40 to 100° C. by blowing a 2.0 to 3.0 equivalence of hydrogen chloride gas through the alcohol compound in the presence of hydrochloric acid. Following completion of the reaction, the target chloromethyl ether compound can be obtained by distillation of the reaction product under reduced pressure.

[Formula 10]

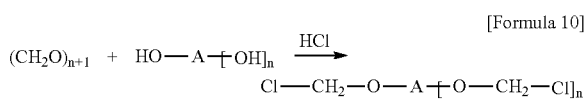

By reacting the chloromethyl ether compound obtained in the above manner with an aforementioned polymer compound or low molecular weight compound containing at least one alkali-soluble group (i) selected from amongst alcoholic hydroxyl groups, phenolic hydroxyl groups and carboxyl groups, the alkali-soluble group (i) is protected with an acid dissociable, dissolution inhibiting group (ii) represented by the aforementioned general formula (1), thus completing preparation of the polymer compound or photoresist composition low molecular weight compound according to the present invention.

Of the polymer compounds and photoresist composition low molecular weight compounds of the present invention, the aforementioned polymer compound containing protected alcoholic hydroxyl groups can be produced, for example, by reacting an aforementioned halogenated methyl ether compound with an aforementioned fluoroalcohol-containing or alcohol-containing polymer. In a similar manner, the low molecular weight compound containing alcoholic hydroxyl groups can be produced by reacting an aforementioned halogenated methyl ether compound with the corresponding fluoroalcohol-containing or alcohol-containing low molecular weight compound.

Of the polymer compounds and low molecular weight compounds for a photoresist composition of the present invention, the aforementioned polymer compound containing protected phenolic hydroxyl groups can be produced, for example, by reacting an aforementioned halogenated methyl ether compound with an aforementioned polyhydroxystyrene resin (15). In a similar manner, the low molecular weight compound containing phenolic hydroxyl groups can be produced by reacting an aforementioned halogenated methyl ether compound with the corresponding low molecular weight polyhydric phenol compound.

Of the polymer compounds and low molecular weight compounds for a photoresist composition of the present invention, the aforementioned polymer compound containing protected carboxyl groups can be produced, for example, by using an unsaturated carboxylate ester, produced by reacting an aforementioned halogenated methyl ether compound with an unsaturated carboxylic acid such as acrylic acid or methacrylic acid, as one monomer, and conducting a polymerization of this monomer with another monomer containing a carboxyl group such as acrylic acid or methacrylic acid. In a similar manner, the low molecular weight compound containing protected carboxyl groups can be produced by reacting an aforementioned halogenated methyl ether compound with an aforementioned bile acid or the like.

<Compounds>

A compound of the third aspect of the present invention (hereafter also referred to as the compound (a)), as shown in the above formula (41), has a structure in which a plurality of methylene groups, formed by removing one hydrogen atom from the methyl group of the ester side-chain portion of a plurality (n+1) of methyl(meth)acrylates, are each bonded to a hydrocarbon group A of 1 to 20 carbon atoms via an oxygen atom. In this description and the associated claims, the term "(meth)acrylate" refers to one or both of a methacrylate and an acrylate.

In the formula (41), $R^1$ and $R^2$ each represent, independently, a hydrogen atom or a methyl group. Furthermore, in those cases where n is an integer from 2 to 4, the n $R^2$ groups within the formula (41) each represent, independently, a hydrogen atom or a methyl group.

In the formula (41), n represents an integer from 1 to 4, and is preferably either 1 or 2, and most preferably 1.

In the formula (41), A represents a hydrocarbon group of 1 to 20 carbon atoms with a valency of (n+1).

This hydrocarbon group may be a straight-chain, branched or cyclic group, or may also be a combination thereof. Furthermore, either a saturated hydrocarbon group that contains no unsaturated bonds, or an unsaturated hydrocarbon group that includes an unsaturated bond is suitable.

Of these possibilities, straight-chain saturated hydrocarbon groups of 1 to 4 carbon atoms are preferred from the viewpoint of industrial availability. The number of carbon atoms within the saturated hydrocarbon group is even more preferably from 1 to 3, and is most preferably either 2 or 3. In those cases in which n is 1, the saturated hydrocarbon group is an alkylene group, and specific examples include a methylene group, ethylene group, n-propylene group, or n-butylene group.

Furthermore, from the viewpoint of etching resistance, a hydrocarbon group containing a cyclic group of 4 to 15 carbon atoms is preferred.

Here, the description "hydrocarbon group containing a cyclic group of 4 to 15 carbon atoms" refers to a hydrocarbon group that includes a cyclic group (a cyclic hydrocarbon group) of 4 to 15 carbon atoms within the structure of the group, and this group may be composed solely of the cyclic hydrocarbon group of 4 to 15 carbon atoms, or may be a group in which a straight-chain hydrocarbon group such as a methylene group or ethylene group is bonded to the cyclic hydrocarbon group. The number of carbon atoms within the cyclic group is even more preferably within a range from 4 to 10, and is most preferably from 4 to 8.

Furthermore, the number of carbon atoms within the hydrocarbon group containing the cyclic group of 4 to 15 carbon atoms is preferably within a range from 4 to 20, and even more preferably from 4 to 10.

The cyclic group of 4 to 15 carbon atoms may be either an aliphatic cyclic group or an aromatic cyclic group. Furthermore, the group may be either a monocyclic group or a polycyclic group.

In this description, the term "aliphatic" is a relative concept used in relation to the term "aromatic", and defines a group or compound that contains no aromaticity. Furthermore, the term "aliphatic cyclic group" (or preferably alicyclic group) describes a monocyclic group or polycyclic group that contains no aromaticity.

As this cyclic group of 4 to 15 carbon atoms, aliphatic cyclic groups are preferred as they yield reduced levels of line edge roughness and favorable cross-sectional rectangular formability within the resist pattern.

Specific examples of aliphatic cyclic groups of 4 to 15 carbon atoms include groups in which two or more carbon atoms have been removed from a cycloalkane, bicycloalkane, bicycloalkene, tricycloalkane, tetracycloalkane, methylbicycloalkane, methylbicycloalkene, methyltricycloalkane, methyltetracycloalkane, ethylbicycloalkane, ethylbicycloalkene, ethyltricycloalkane, or ethyltetracycloalkane or the like.

Specific examples include groups in which two or more hydrogen atoms have been removed from cyclohexane, cyclopentane, or a polycycloalkane such as adamantane, norbornane, norbornene, methylnorbornane, ethylnorbornane, methylnorbornene, ethylnorbornene, isobornane, tricyclodecane or tetracyclododecane. These types of polycyclic groups can be selected appropriately from the multitude of groups proposed for use within ArF resists.

Of the various possibilities, groups in which two or more hydrogen atoms have been removed from a cyclic saturated hydrocarbon group such as cyclohexane, cyclopentane, adamantane or norbornane (namely, cyclic saturated hydrocarbon groups) are preferred in terms of the resulting resolution, and the group in which two hydrogen atoms have been removed from cyclohexane are particularly desirable.

Furthermore, examples of aromatic cyclic groups of 4 to 15 carbon atoms include groups in which two or more hydrogen atom have been removed from naphthalene, anthracene, or phenanthrene or the like.

Cases in which the compound (a) is a compound represented by either of the general formulas (42) and (43) shown below yield superior effects for the present invention, and are consequently preferred.

[Formula 11]

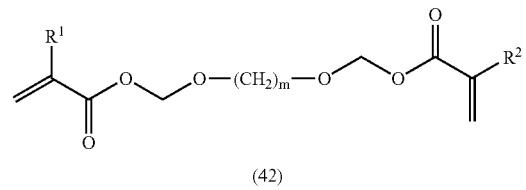

(42)

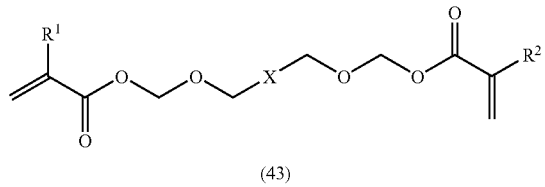

(43)

[wherein, $R^1$ and $R^2$ each represent, independently, a hydrogen atom or a methyl group; m represents an integer from 1 to 3, and preferably either 2 or 3; and X represents a cyclic saturated hydrocarbon group of 4 to 15, and preferably from 4 to 8, carbon atoms]

More specific examples of the compounds represented by the above general formulas (42) and (43) include the compounds represented by the general formulas (44), (45) and (46) shown below.

[Formula 12]

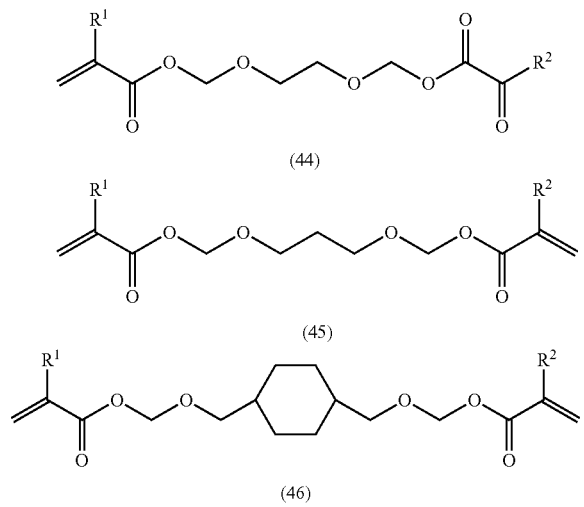

[wherein, $R^1$ and $R^2$ each represent, independently, a hydrogen atom or a methyl group]

The compound (a) according to the present invention can be synthesized by known methods, and can be produced, for example, by synthesizing a halogenated methyl ether compound represented by a general formula shown below:

[wherein, A and n are as defined above, and Z represents a halogen atom (such as a chlorine or bromine atom)], and then reacting this halogenated methyl ether compound with (meth) acrylic acid.

The halogenated methyl ether compound can be synthesized using a method represented by the reaction formula shown below. In other words, paraformaldehyde is added to an alcohol compound represented by HO-A-[OH]$_n$, and a reaction is then conducted at 40 to 100° C. by blowing a 2.0 to 3.0 equivalence of hydrogen halide gas through the alcohol compound in the presence of hydrochloric acid. Following completion of the reaction, the target halogenated methyl ether compound can be obtained by distillation of the reaction product under reduced pressure.

[Formula 13]

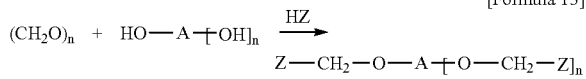

[wherein, A, n and Z are as defined above]

The compound (a) of the present invention can be used favorably for producing the polymer compound of the present invention described below.

<Polymer Compound>

The polymer compound according to a second aspect of the present invention (hereafter also referred to as the polymer compound (A)) is characterized by including a structural unit (a1) represented by the general formula (51) shown above.

The $—CH_2—O-A-[O—CH_2—]_s$ group within the structural unit (a1) acts as an acid dissociable, dissolution inhibiting group. Accordingly, when acid generated from the acid generator component by exposure acts upon the polymer compound (A), the $—CH_2—O-A-[O—CH_2—]_s$ acid dissociable, dissolution inhibiting group dissociates, causing the entire polymer compound (A) to change from an alkali-insoluble state to an alkali-soluble state.

As a result, when a resist is exposed through a mask pattern during the formation of a resist pattern, or alternatively, is exposed and then subjected to post exposure baking, the exposed portions of the resist shift to an alkali-soluble state, whereas the unexposed portions remain insoluble in alkali, meaning that alkali developing can then be used to form a positive resist pattern.

—Structural Unit (a1)

The groups $R^1$ and $R^2$ in the formula (51) have the same meaning as the groups $R^1$ and $R^2$ within the general formula (41) described above.

Furthermore, the value of s in the formula (51) has the same meaning as n within the general formula (41) described above.

A represents an organic group with a valency of (s+1). There are no particular restrictions on this organic group, and suitable groups include hydrocarbon groups formed from carbon atoms (C) and hydrogen atoms (H) (including saturated or unsaturated aromatic or aliphatic hydrocarbon groups such as alkylene groups and arylene groups), as well as groups that also contain additional hetero atoms, including groups containing C, H, and an oxygen atom (O) (such as ether groups, polyether groups and ester groups), and groups containing C, H, and a nitrogen atom (N).

Of these possibilities, from the viewpoint of achieving superior effects for the present invention, A is preferably a hydrocarbon group of 1 to 20 carbon atoms with a valency of (n+1). In other words, the structural unit (a1) is preferably a structural unit (a1-1) derived from the compound (a).

The description "structural unit derived from the compound (a)" refers to a structural unit that is formed by cleavage of the ethylenic double bond of the compound (a).

The proportion of the structural unit (a1) within the polymer compound (A), relative to the combined total of all the structural units that constitute the polymer compound (A), is preferably at least 1 mol %, more preferably within a range from 3 to 50 mol %, and even more preferably from 3 to 30 mol %. Ensuring this proportion is at least 1 mol % enables the effects of the present invention to manifest adequately. Furthermore, provided the upper limit for the proportion of the structural unit (a1) is no higher than 50 mol %, favorable solubility within organic solvents can be achieved. Furthermore, the removability of the resist pattern also improves. Resist pattern collapse can also be suppressed.

Structural Unit (a2)

In addition to the structural unit (a1) described above, the polymer compound (A) preferably also includes a structural unit (a2) derived from a mono (α-lower alkyl)acrylate ester containing an acid dissociable, dissolution inhibiting group. Including such a structural unit further improves the resolution.

In this description, the term "mono" within the term "mono (α-lower alkyl)acrylate ester" describes the inclusion of one (α-lower alkyl)acrylate ester residue represented by the general formula shown below.

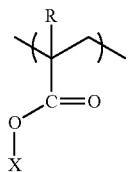

[Formula 14]

[wherein, R represents a hydrogen atom or a lower alkyl group, and X represents a monovalent organic group]

Furthermore, the term "(α-lower alkyl)acrylate ester" is a generic term that describes α-lower alkyl acrylate esters such as one or both of a methacrylate ester and an acrylate ester.

The term "α-lower alkyl acrylate ester" refers to a structure in which the hydrogen atom bonded to the α-carbon atom of an acrylate ester has been substituted with a lower alkyl group.

There are no particular restrictions on the "lower alkyl group" of a α-lower alkyl acrylate ester, although straight-chain or branched alkyl groups of 1 to 5 carbon atoms are preferred, and suitable examples include a methyl group, ethyl group, propyl group, isopropyl group, n-butyl group, isobutyl group, tert-butyl group, pentyl group, isopentyl group or neopentyl group, although a methyl group is preferred from an industrial viewpoint.

A "structural unit derived from a mono (α-lower alkyl) acrylate ester" refers to a structural unit formed by cleavage of the ethylenic double bond of a mono (α-lower alkyl)acrylate ester.

There are no particular restrictions on the acid dissociable, dissolution inhibiting group within the structural unit (a2). Generally, groups that form a cyclic or chain-like tertiary alkyl ester with the carboxyl group of the (α-lower alkyl) acrylic acid are the most widely known, but from the viewpoints of dry etching resistance and achieving a favorable resist pattern shape, the use of a monocyclic or polycyclic alicyclic group-containing acid dissociable, dissolution inhibiting group is preferred. Furthermore, groups that form an alkoxymethyl ester containing a cyclic or chain-like alkyl group with the carboxyl group of the (α-lower alkyl)acrylic acid can also be used.

Examples of monocyclic alicyclic groups include groups in which one hydrogen atom has been removed from a monocycloalkane such as cyclohexane or cyclopentane.

Examples of polycyclic alicyclic groups include groups in which either one or two hydrogen atoms have been removed from a bicycloalkane, tricycloalkane or tetracycloalkane, and specific examples include groups in which either one or two hydrogen atoms have been removed from adamantane, norbornane, isobornane, tricyclodecane or tetracyclododecane.

These types of monocyclic or polycyclic alicyclic groups can be selected appropriately from the multitude of groups proposed for use in the resin components of resist compositions for use with KrF excimer lasers and ArF excimer lasers.

Of these, a cyclohexyl group, cyclopentyl group, adamantyl group, norbornyl group or tetracyclododecanyl group is preferred in terms of industrial availability.

More specific examples of the structural unit (a2) include structural units derived from a mono (α-lower alkyl)acrylate ester containing a monocyclic alicyclic group-containing acid dissociable, dissolution inhibiting group, such as the structural units represented by a general formula (60) shown below, structural units (a2-1) derived from a mono (α-lower alkyl)acrylate ester containing a polycyclic alicyclic group-containing acid dissociable, dissolution inhibiting group, such as the structural units represented by general formulas (61), (62) and (63) shown below, and structural units (a2-2) represented by general formulas (64), (65) and (66) shown below.

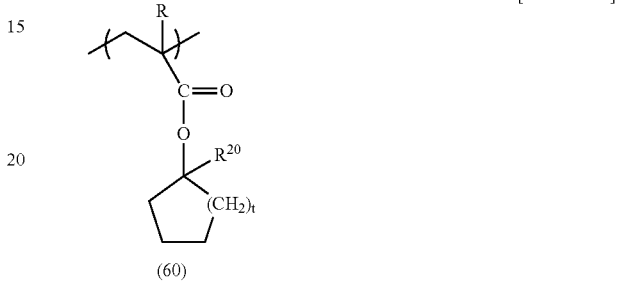

[Formula 15]

(60)

[In the formula (60), R represents a hydrogen atom or a lower alkyl group, $R^{20}$ represents a lower alkyl group, and t represents an integer from 1 to 3.]

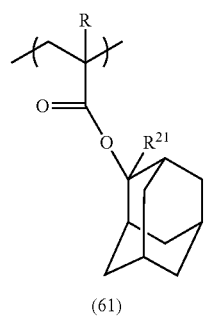

(61)

[In the formula (61), R represents a hydrogen atom or a lower alkyl group, and $R^{21}$ represents a lower alkyl group.]

[Formula 17]

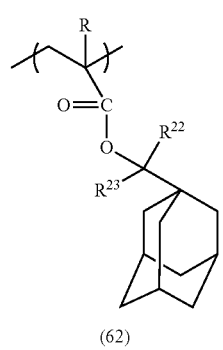

(62)

[In the formula (62), R represents a hydrogen atom or a lower alkyl group, and $R^{22}$ and $R^{23}$ each represent, independently, a lower alkyl group.]

[Formula 18]

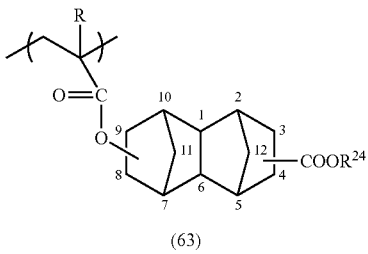

(63)

[In the formula (63), R represents a hydrogen atom or a lower alkyl group, and $R^{24}$ represents a tertiary alkyl group.]

[Formula 19]

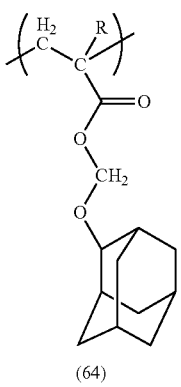

(64)

[In the formula (64), R represents a hydrogen atom or a lower alkyl group.]

[Formula 20]

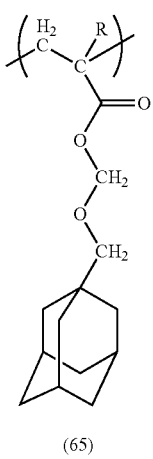

(65)

[In the formula (65), R represents a hydrogen atom or a lower alkyl group.]

[Formula 21]

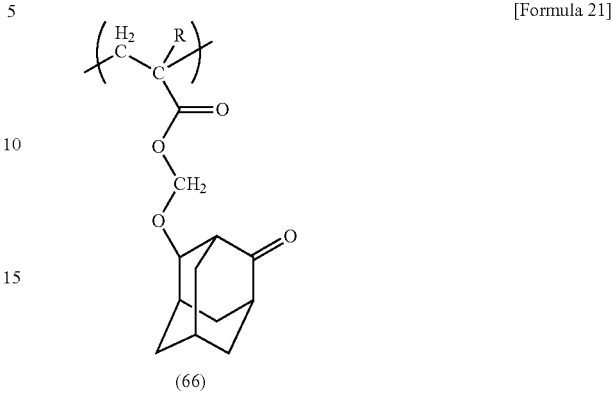

(66)

[In the formula (66), R represents a hydrogen atom or a lower alkyl group.]

In the formula (60), the group $R^{20}$ is preferably a lower straight-chain or branched alkyl group of 1 to 5 carbon atoms, and suitable examples include a methyl group, ethyl group, propyl group, isopropyl group, n-butyl group, isobutyl group, pentyl group, isopentyl group, and neopentyl group. Of these, alkyl groups of 2 or more, and preferably from 2 to 5, carbon atoms are particularly preferred, and such groups tend to yield better acid dissociability than the case of a methyl group. From an industrial viewpoint, a methyl group or ethyl group is preferred.

In the formula (61), the group $R^{21}$ is preferably a lower straight-chain or branched alkyl group of 1 to 5 carbon atoms, and suitable examples include a methyl group, ethyl group, propyl group, isopropyl group, n-butyl group, isobutyl group, pentyl group, isopentyl group, and neopentyl group. Of these, alkyl groups of 2 or more, and preferably from 2 to 5, carbon atoms are particularly preferred, and such groups tend to yield better acid dissociability than the case of a methyl group. From an industrial viewpoint, a methyl group or ethyl group is preferred.

In the formula (62), the groups $R^{22}$ and $R^{23}$ preferably each represent, independently, a lower alkyl group of 1 to 5 carbon atoms. The acid dissociable, dissolution inhibiting group represented by the formula (62) tends to exhibit better acid dissociability than a 2-methyl-2-adamantyl group.

More specifically, the groups $R^{22}$ and $R^{23}$ preferably each represent the same type of lower straight-chain or branched alkyl group as those described above for the group $R^{21}$. Of these, the case in which $R^{22}$ and $R^{23}$ are both methyl groups is preferred industrially, and a specific example of the structural unit represented by the formula (62) is the structural unit derived from 2-(1-adamantyl)-2-propyl(meth)acrylate.

In the formula (63), the group $R^{24}$ represents a tertiary alkyl group of 4 or 5 carbon atoms such as a tert-butyl group or tert-amyl group, although the case in which $R^{24}$ is a tert-butyl group is preferred industrially.

Furthermore, the group —COOR$^{24}$ may be bonded to either position 3 or 4 of the tetracyclododecanyl group shown in the formula, although a mixture of both isomers results, and so the bonding position cannot be further specified. Furthermore, the carboxyl group residue of the mono (α-lower alkyl) acrylate ester may be bonded to either position 8 or 9 of the tetracyclododecanyl group, although similarly, a mixture of both isomers results, and so the bonding position cannot be further specified.

In the polymer compound (A), the proportion of the structural unit (a2), relative to the combined total of all the structural units that constitute the polymer compound (A), is preferably within a range from 10 to 80 mol %, and even more preferably from 20 to 60 mol %. Ensuring this proportion is at least 10 mol %, and preferably 20 mol or greater, enables the resolution to be further improved when the compound is used in a resist composition, whereas by ensuring the proportion is no greater than 80 mol %, and preferably 60 mol % or less, a more favorable quantitative balance can be achieved with the other structural units (and therefore a more favorable balance of physical properties).

—Structural Unit (a3)

In addition to the aforementioned structural unit (a1), or in addition to the structural unit (a1) and the structural unit (a2), the polymer compound (A) preferably also includes a structural unit (a3) derived from a mono (α-lower alkyl)acrylate ester that contains a lactone-containing monocyclic or polycyclic group. Including such a structural unit improves the adhesion between the resist film and the substrate, and inhibits the occurrence of pattern collapse and film peeling and the like within fine resist patterns. Furthermore, the hydrophilicity of the polymer compound (A) is also enhanced, thereby improving the affinity with the developing solution, improving the alkali solubility within the exposed portions of the resist, and contributing to further improvement in the resolution.

Examples of the structural unit (a3) include structural units in which a monocyclic group composed of a lactone ring, or a polycyclic alicyclic group containing a lactone ring, is bonded to the ester side chain portion of a mono (α-lower alkyl)acrylate ester. The term "lactone ring" refers to a single ring containing a —O—C(O)— structure, and this ring is counted as the first ring. Accordingly, the case in which the only ring structure is the lactone ring is referred to as a monocyclic group, and groups containing other ring structures are described as polycyclic groups regardless of the structure of the other rings.

Examples of the structural unit (a3) include monocyclic groups in which one hydrogen atom has been removed from γ-butyrolactone, and polycyclic groups in which one hydrogen atom has been removed from a lactone ring-containing polycycloalkane.

Specific examples include structural units derived from a mono (α-lower alkyl)acrylate ester containing a monocyclic group composed of a monocyclic lactone ring, such as the structural units represented by a general formula (71) shown below, and structural units derived from a mono (α-lower alkyl)acrylate ester containing a polycyclic alicyclic group that contains a lactone ring, such as the structural units represented by formulas (72) through (75) shown below.

Of these, structural units represented by the formula (71) are preferred, as they yield particularly superior resolution and also yield excellent lithography properties such as the depth of focus, and structural units that contain the ester linkage at the α-carbon of the lactone skeleton, and in which $R^{31}$ and $R^{32}$ are hydrogen atoms, namely, structural units derived from a mono (α-lower alkyl)acrylate ester of γ-butyrolactone, are particularly desirable.

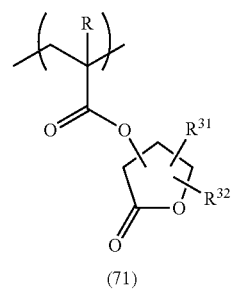

[Formula 22]

(71)

[In the formula (71), R represents a hydrogen atom or a lower alkyl group, and $R^{31}$ and $R^{32}$ each represent, independently, a hydrogen atom or a lower alkyl group.]

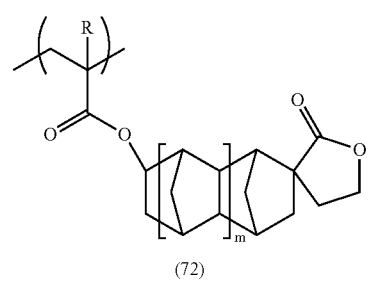

[Formula 23]

(72)

[wherein, R is as defined above, and m represents either 0 or 1]

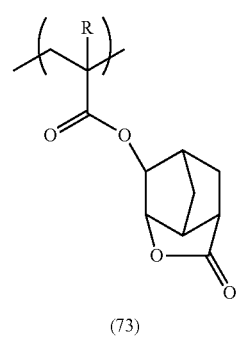

[Formula 24]

(73)

[wherein, R is as defined above]

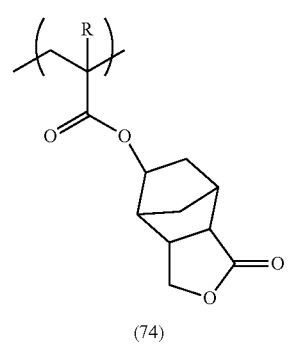

[Formula 25]

(74)

[wherein, R is as defined above]

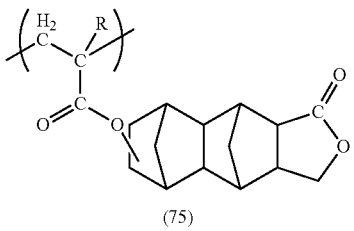

(75)

[Formula 26]

[wherein, R is as defined above]

The proportion of the structural unit (a3), relative to the combined total of all the structural units that constitute the polymer compound (A), is preferably within a range from 10 to 75 mol %, and even more preferably from 20 to 70 mol %, and most preferably from 30 to 70 mol %.

In addition to the structural units (a1), (a2) and (a3) described above, the polymer compound (A) may also include other structural units, provided their inclusion does not impair the effects of the present invention. Examples of such other structural units include the structural units (a4) through (a6) described below.

Structural unit (a4): a structural unit derived from a mono (α-lower alkyl)acrylate ester that contains a polar group-containing aliphatic hydrocarbon group Structural unit (a5): a structural unit derived from a mono (α-lower alkyl)acrylate ester containing a polycyclic aliphatic hydrocarbon group that is different from the structural units (a2) through (a4)

Structural unit (a6): a structural unit derived from a mono (α-lower alkyl)acrylic acid Structural Unit (a4)

The structural unit (a4) is a structural unit derived from a (meth)acrylate ester that contains a polar group-containing aliphatic hydrocarbon group. Including such structural units increases the hydrophilicity of the overall polymer compound (A), thereby improving the affinity with the developing solution, improving the alkali solubility within the exposed portions of the resist, and contributing to improvement in the resolution.

Examples of the polar group include a hydroxyl group or cyano group or the like, although a hydroxyl group is particularly preferred.

Examples of the aliphatic hydrocarbon group include straight-chain or branched hydrocarbon groups (alkylene groups) of 1 to 10 carbon atoms, and polycyclic aliphatic hydrocarbon groups (polycyclic groups). These polycyclic groups can be selected appropriately from the same multitude of groups described above in relation to the structural unit (a2).

When the hydrocarbon group within the polar group-containing aliphatic hydrocarbon group is a straight-chain or branched hydrocarbon group of 1 to 10 carbon atoms, the structural unit (a4) is preferably a structural unit derived from the hydroxyethyl ester of (meth)acrylic acid, whereas when the hydrocarbon group is a polycyclic group, structural units represented by formulas (81) and (82) shown below are preferred.

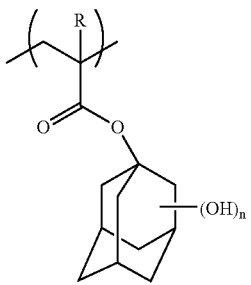

(81)

[Formula 27]

(wherein, R is as defined above, and n represents an integer from 1 to 3)

Of these, structural units in which n is 1, and the hydroxyl group is bonded to position 3 of the adamantyl group are preferred.

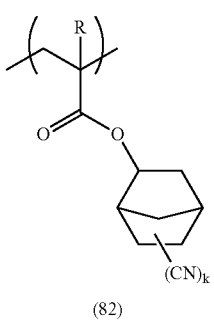

(82)

(wherein, R is as defined above, and k represents an integer from 1 to 3)

Of these, structural units in which k is 1 are preferred. These structural units exist as a mixture of isomers (that is, a mixture of compounds in which the cyano group is bonded to either position 4 or position 5 of the norbornyl group).

The proportion of the structural unit (a4), relative to the combined total of all the structural units that constitute the polymer compound (A), is preferably within a range from 10 to 50 mol %, and even more preferably from 20 to 40 mol %.

Structural Unit (a5)

The structural unit (a5) is a structural unit derived from a mono (α-lower alkyl)acrylate ester containing a polycyclic aliphatic hydrocarbon group that is different from the structural units (a2) through (a4).

Here, the expression "different from the structural units (a2) through (a4)" means these units do not duplicate the structural units (a2) through (a4), although examples of the polycyclic aliphatic hydrocarbon group (hereafter also referred to as simply "the polycyclic group") include the same multitude of polycyclic groups described above in relation to the structural units (a1) through (a4). In terms of industrial availability and the like, one or more groups selected from amongst a tricyclodecanyl groups, adamantyl group, and tetracyclododecanyl group is preferred.

Specific examples of the structural unit (a5) include units of the structures represented by the formulas (91) through (93) shown below.

[Formula 29]

(91)

(wherein, R is as defined above)

[Formula 30]

(92)

(wherein, R is as defined above)

[Formula 31]

(93)

(wherein, R is as defined above)

The proportion of the structural unit (a5), relative to the combined total of all the structural units that constitute the polymer compound (A), is preferably within a range from 3 to 50 mol %, and even more preferably from 5 to 35 mol %.

In addition to the structural units described above, a polymer compound (A) of the present invention may also contain the types of structural units typically included within the resin component of conventional resist compositions for use with KrF excimer lasers or ArF excimer lasers or the like, including structural units derived from (α-methyl)styrene and structural units derived from (α-methyl)hydroxystyrene, provided the inclusion of such units does not impair the effects of the present invention.

A structural unit derived from (α-methyl)styrene refers to a structural unit formed by cleavage of the ethylenic double bond of the (α-methyl)styrene, whereas a structural unit derived from (α-methyl)hydroxystyrene refers to a structural unit formed by cleavage of the ethylenic double bond of the (α-methyl)hydroxystyrene.

Furthermore, the term "(α-methyl)styrene" is a generic term that describes styrene and/or α-methylstyrene, whereas the term "(α-methyl)hydroxystyrene" is a generic term that describes one or both of hydroxystyrene and α-methylhydroxystyrene.

In the polymer compound (A), the combination of structural units such as the structural unit (a1) and the respective proportions of each of the structural units can be adjusted appropriately in accordance with the properties desired. In consideration of the shape and resolution and the like of the obtained resist pattern, the polymer compound preferably includes the structural unit (a1), the structural unit (a2), and/or the structural unit (a3), and compounds that include all of the structural units (a1) through (a3) are particularly desirable.

Specific examples of preferred forms of the polymer compound (A) include copolymers that include the structural units represented by the general formulas (A1) through (A4) shown below, and one or more of these copolymers can be used as the polymer compound (A).

[Formula 32]

(A1)

[wherein, R represents a hydrogen atom or a methyl group]

[Formula 33]

(A2)

[wherein, R represents a hydrogen atom or a methyl group]

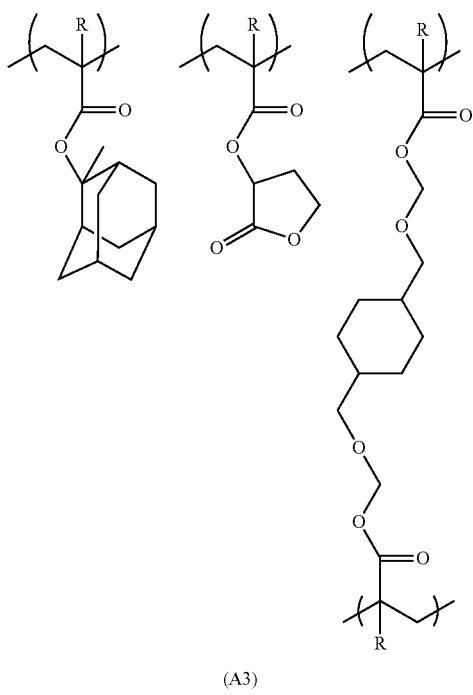

(A3)

[wherein, R represents a hydrogen atom or a methyl group]

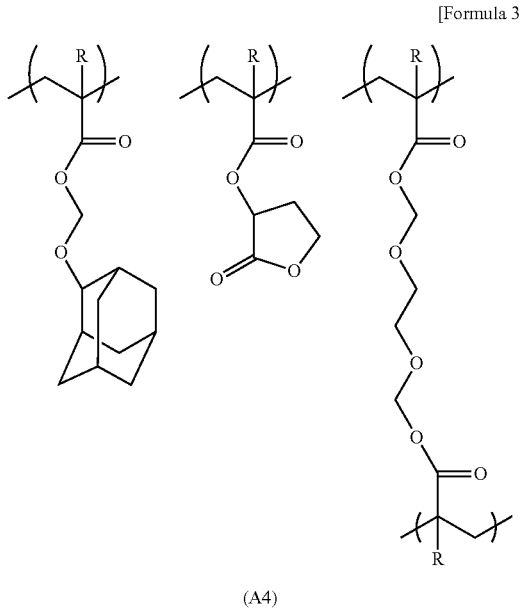

(A4)

[wherein, R represents a hydrogen atom or a methyl group]

The polymer compound (A) can be produced, for example, by a conventional radical polymerization or the like of the monomers corresponding with each of the structural units, using a radical polymerization initiator such as azobisisobutyronitrile (AIBN).

Although there are no particular restrictions on the weight average molecular weight (the polystyrene equivalent value determined by gel permeation chromatography, this also applies below) of the polymer compound (A), in those cases where the compound is used in a positive resist composition, the weight average molecular weight is preferably within a range from 2,000 to 50,000, and even more preferably from 5,000 to 30,000.

A polymer compound of the first aspect of the present invention or a polymer compound (A) of the second aspect are ideal as the base resin component of a positive resist composition.

<Positive Resist Composition>

A positive resist composition of the present invention includes either an aforementioned polymer compound of the first aspect of the present invention (hereafter referred to as the polymer compound (AA)) or an aforementioned polymer compound of the second aspect of the present invention (hereafter, these compounds may also be referred to as the component (A)), and an acid generator component (B) that generates acid on exposure (irradiation with some form of radiation) (hereafter also referred to as the component (B)).

Component (A)

The component (A) is either of the aforementioned polymer compounds (AA) and (A) of the present invention, and these polymer compounds (AA) or (A) may be used either alone, or in combinations of two or more different compounds.

When a polymer compound (AA) or (A) such as those described above is used within a chemically amplified positive resist system of the present invention, because the polymer compound contains hydrophilic acid dissociable, dissolution inhibiting groups represented by the above formula (1), the compound exhibits a powerful alkali solubility inhibiting effect prior to exposure, but following the exposure and PEB processes, the compound develops alkali solubility as a result of the deprotection of these acid dissociable, dissolution inhibiting groups, meaning the alkali solubility changes significantly from the state prior to exposure to that following exposure, thereby enabling a fine pattern with a high level of resolution to be provided. Furthermore, thickness loss of the resist pattern can also be prevented.

The proportion of the polymer compound (A) within the positive resist composition can be altered appropriately in accordance with the desired resist film thickness.

In the present invention, other polymer compounds (hereafter referred to as polymer compounds (A')) such as polyhydroxystyrene resins or (meth)acrylate resins that have been proposed as base resin components within conventional positive resist compositions may also be included in addition to the polymer compound (A), although in order to maximize the effects of the present invention, the proportion of the polymer compound (A) relative to the combination of the polymer compound (A) and the polymer compounds (A') is preferably at least 80% by weight, even more preferably 90% by weight, and is most preferably 100% by weight.

Component (B)

As the component (B), a compound appropriately selected from amongst conventional acid generators can be used. Examples of these acid generators are numerous, and include onium salt-based acid generators such as iodonium salts and sulfonium salts, oxime sulfonate-based acid generators, diazomethane-based acid generators such as bisalkyl or bisaryl sulfonyl diazomethanes, poly(bis-sulfonyl)diazomethanes and diazomethane nitrobenzyl sulfonates, iminosulfonate-based acid generators, and disulfone-based acid generators.

Specific examples of suitable onium salt-based acid generators include diphenyliodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl) diphenylsulfonium trifluoromethanesulfonate, heptafluoropropanesulfonate or nonafluorobutanesulfonate, and tri(4-tert-butyl)phenylsulfonium trifluoromethanesulfonate, heptafluoropropanesulfonate or nonafluorobutanesulfonate. Of these, onium salts with a fluorinated alkylsulfonate ion as the anion are preferred.

Furthermore, in the present invention, onium salts with a camphorsulfonate ion as the anion, which generate an acid of weaker acidity than that generated by an onium salt with a fluorinated alkylsulfonate ion as the anion, can also be used as an onium salt-based acid generator. A specific example of such a salt is the compound represented by a chemical formula (b-1) shown below.

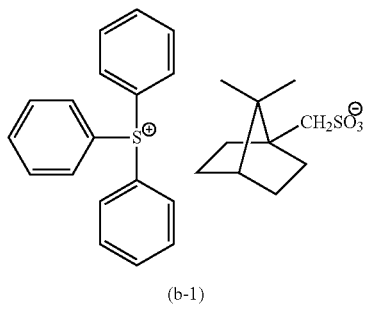

[Formula 36]

(b-1)

Specific examples of suitable oxime sulfonate-based acid generators include α-(p-toluenesulfonyloxyimino)-benzyl cyamide, α-(p-chlorobenzenesulfonyloxyimino)-benzyl cyamide, α-(4-nitrobenzenesulfonyloxyimino)-benzyl cyamide, α-(4-nitro-2-trifluoromethylbenzenesulfonyloxyimino)-benzyl cyamide, α-(benzenesulfonyloxyimino)-4-chlorobenzyl cyamide, α-(benzenesulfonyloxyimino)-2,4-dichlorobenzyl cyamide, α-(benzenesulfonyloxyimino)-2,6-dichlorobenzyl cyamide, α-(benzenesulfonyloxyimino)-4-methoxybenzyl cyamide, α-(2-chlorobenzenesulfonyloxyimino)-4-methoxybenzyl cyamide, α-(benzenesulfonyloxyimino)-thien-2-yl acetonitrile, α-(4-dodecylbenzenesulfonyloxyimino)benzyl cyamide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyamide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-1-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile. Of these, α-(methylsulfonyloxyimino)-p-methoxyphenyl acetonitrile is preferred.

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Furthermore, specific examples of poly(bis-sulfonyl)diazomethanes include the structures shown below, such as 1,3-bis(phenylsulfonyldiazomethylsulfonyl)propane (compound A, decomposition point 135° C.), 1,4-bis(phenylsulfonyldiazomethylsulfonyl)butane (compound B, decomposition point 147° C.), 1,6-bis(phenylsulfonyldiazomethylsulfonyl)hexane (compound C, melting point 132° C., decomposition point 145° C.), 1,10-bis(phenylsulfonyldiazomethylsulfonyl)decane (compound D, decomposition point 147° C.), 1,2-bis(cyclohexylsulfonyldiazomethylsulfonyl)ethane (compound E, decomposition point 149° C.), 1,3-bis(cyclohexylsulfonyldiazomethylsulfonyl)propane (compound F, decomposition point 153° C.), 1,6-bis(cyclohexylsulfonyldiazomethylsulfonyl)hexane (compound G, melting point 109° C., decomposition point 122° C.), and 1,10-bis(cyclohexylsulfonyldiazomethylsulfonyl)decane (compound H, decomposition point 116° C.).

[Formula 37]

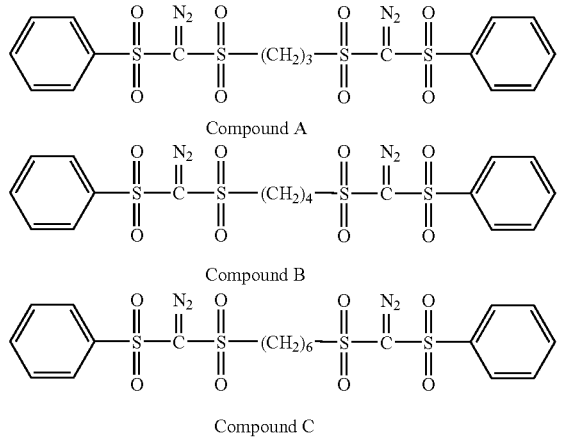

Compound A

Compound B

Compound C

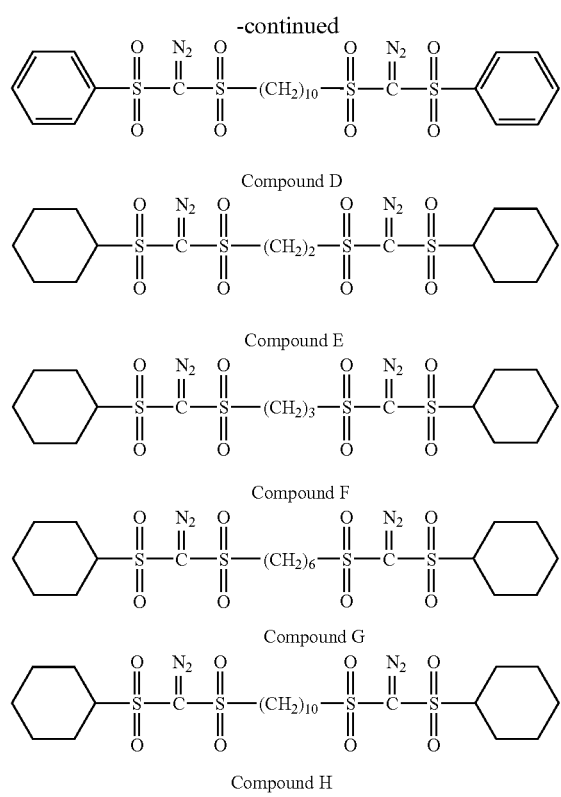

Compound D

Compound E

Compound F

Compound G

Compound H

As the component (B), either a single acid generator may be used alone, or a combination of two or more different acid generators may be used.

The quantity used of the component (B) is typically within a range from 0.5 to 30 parts by weight, and preferably from 1 to 10 parts by weight, per 100 parts by weight of the component (A). At quantities less than the above range, there is a danger that pattern formation may not proceed satisfactorily, whereas if the quantity exceeds the above range, achieving a uniform solution becomes difficult, and there is a danger of a deterioration in the storage stability.

Furthermore, this photoresist composition may also include an aforementioned low molecular weight compound for a photoresist composition as an acid dissociable, dissolution inhibitor (C).

If the type of low molecular weight compound described above is used in a chemically amplified positive resist system of the present invention, then because the low molecular weight compound contains a hydrophilic acid dissociable group represented by the above general formula (1), the compound exhibits an inhibiting effect upon alkali developing prior to exposure, but then following the exposure and PEB processes, develops alkali solubility as a result of deprotection, meaning the alkali solubility changes significantly from the state prior to exposure to that following exposure, thereby enabling a fine pattern with a high level of resolution to be provided. Furthermore, thickness loss of the resist pattern can also be prevented.

The acid dissociable, dissolution inhibitor (C) described above is typically used in a quantity within a range from 3 to 50 parts by weight, and preferably from 5 to 30 parts by weight, per 100 parts by weight of the base resin component (A). If the quantity is less than this range, then improvements in the resolution and pattern shape cannot be achieved. In contrast if the quantity is too large, an improvement in the pattern shape is not obtained, and there is also a danger of an undesirable deterioration in the storage stability of the photoresist coating solution.

Component (D)

In a positive resist composition of the present invention, in order to improve the resist pattern shape and the post exposure stability of the latent image formed by the pattern-wise exposure of the resist layer, a nitrogen-containing organic compound (D) (hereafter referred to as the component (D)) can be added as an optional component.

A multitude of these components (D) have already been proposed, and any of these known compounds can be used, although an amine or an ammonium salt, and particularly a secondary lower aliphatic amine or tertiary lower aliphatic amine is preferred.

Examples of the aforementioned amine include aliphatic secondary amines such as diethylamine, dipropylamine, dibutylamine and dipentylamine, aliphatic tertiary amines such as trimethylamine, triethylamine, tripropylamine, tributylamine, tripentylamine, N,N-dimethylpropylamine, N-ethyl-N-methylbutylamine, trihexylamine, triheptylamine, trioctylamine, tridecanylamine, tridodecylamine and tritetradecanylamine (in these trialkylamines, the three alkyl groups bonded to the nitrogen atom may be either the same or different), tertiary alkanolamines such as N,N-dimethylmonoethanolamine, triisopropanolamine, N,N-diethylmonoethanolamine, triethanolamine and tributanolamine, and aromatic tertiary amines such as N,N-dimethylaniline, N,N-diethylaniline, N-ethyl-N-methylaniline, N,N-dimethyltoluidine, N-methyldiphenylamine, N-ethyldiphenylamine and triphenylamine.

Examples of the aforementioned ammonium salts include salts containing an ammonium ion or quaternary alkylammonium ion such as a tetramethylammonium ion, tetraethylammonium ion, tetrapropylammonium ion, tetrabutylammonium ion or tetrapentylammonium ion, together with an anion of an organic carboxylic acid that includes a hydroxyl group such as lactic acid.

Of the above possibilities, lower tertiary alkanolamines such as triethanolamine, triisopropanolamine and tributanolamine, and trialkylamines containing from 6 to 15 carbon atoms such as trihexylamine, triheptylamine, trioctylamine, tridecanylamine, tridodecylamine and tritetradecanylamine exhibit superior results in terms of reducing thickness loss at the top portions of fine resist patterns, and are consequently preferred.

The nitrogen-containing organic compound (D) is typically used in a quantity within a range from 0.01 to 5 parts by weight per 100 parts by weight of the base resin component (A). If this quantity is less than the above range, then improvements in the pattern shape arising from the effect of the compound in suppressing diffusion of the acid generated by the exposure cannot be achieved, whereas if the quantity is too large, diffusion of the acid is overly suppressed, causing an undesirable deterioration in the so-called exposure sensitivity.

Furthermore, in order to prevent any deterioration in sensitivity caused by the addition of the aforementioned nitrogen-containing organic compound (D), an organic carboxylic acid, or a phosphorus oxo acid or derivative thereof may also be added to a photoresist composition of the present invention as another optional component.

Examples of suitable organic carboxylic acids include malonic acid, citric acid, malic acid, succinic acid, benzoic acid, and salicylic acid.

Examples of suitable phosphorus oxo acids or derivatives thereof include phosphoric acid or derivatives thereof such as esters, including phosphoric acid, di-n-butyl phosphate and diphenyl phosphate; phosphonic acid or derivatives thereof such as esters, including phosphonic acid, dimethyl phosphonate, di-n-butyl phosphonate, phenylphosphonic acid, diphenyl phosphonate, and dibenzyl phosphonate; and phosphinic acid or derivatives thereof such as esters, including phosphinic acid and phenylphosphinic acid, and of these, phosphonic acid is particularly preferred. This organic carboxylic acid, or a phosphorus oxo acid or derivative thereof is typically used in a quantity within a range from 0.01 to 5.0 parts by weight per 100 parts by weight of the resin component (A).

Component E

Furthermore, in order to prevent any deterioration in sensitivity caused by the addition of the aforementioned component (D), and improve the resist pattern shape and the post exposure stability of the latent image formed by the pattern-wise exposure of the resist layer, an organic carboxylic acid, or a phosphorus oxo acid or derivative thereof (E) (hereafter referred to as the component (E)) can also be added as another optional component. The component (D) and the component (E) can be used in combination, or either one may also be used alone.

Examples of suitable organic carboxylic acids include malonic acid, citric acid, malic acid, succinic acid, benzoic acid, and salicylic acid.

Examples of suitable phosphorus oxo acids or derivatives thereof include phosphoric acid or derivatives thereof such as esters, including phosphoric acid, di-n-butyl phosphate and diphenyl phosphate; phosphonic acid or derivatives thereof such as esters, including phosphonic acid, dimethyl phosphonate, di-n-butyl phosphonate, phenylphosphonic acid, diphenyl phosphonate, and dibenzyl phosphonate; and phosphinic acid or derivatives thereof such as esters, including phosphinic acid and phenylphosphinic acid, and of these, phosphonic acid is particularly preferred.

This component (E) is typically used in a quantity within a range from 0.01 to 5.0 parts by weight per 100 parts by weight of the component (A).

Other Optional Components

Other miscible additives can also be added to a positive resist composition of the present invention according to need, including additive resins for improving the properties of the resist film, surfactants for improving the ease of application, dissolution inhibitors, plasticizers, stabilizers, colorants, and halation prevention agents.

Organic Solvent

A positive resist composition of the present invention can be produced by dissolving the materials in an organic solvent.

The organic solvent may be any solvent capable of dissolving the various components to generate a uniform solution, and one or more solvents selected from known materials used as the solvents for conventional chemically amplified resists can be used.

Specific examples of the solvent include γ-butyrolactone; ketones such as acetone, methyl ethyl ketone, cyclohexanone, methyl isoamyl ketone and 2-heptanone; polyhydric alcohols and derivatives thereof such as ethylene glycol, ethylene glycol monoacetate, diethylene glycol, diethylene glycol monoacetate, propylene glycol, propylene glycol monoacetate, dipropylene glycol, or the monomethyl ether, monoethyl ether, monopropyl ether, monobutyl ether or monophenyl ether of dipropylene glycol monoacetate; cyclic ethers such as dioxane; and esters such as methyl lactate, ethyl lactate (EL), methyl acetate, ethyl acetate, butyl acetate, methyl pyruvate, ethyl pyruvate, methyl methoxypropionate, and ethyl ethoxypropionate.

These organic solvents can be used either alone, or as a mixed solvent of two or more different solvents.

Furthermore, mixed solvents of propylene glycol monomethyl ether acetate (PGMEA) and a polar solvent are preferred. The blend ratio (weight ratio) in such mixed solvents can be set in accordance with factors such as the co-solubility of the PGMEA and the polar solvent, but is preferably within a range from 1:9 to 9:1, and even more preferably from 2:8 to 8:2.

More specifically, in those cases where EL is added as the polar solvent, the weight ratio PGMEA:EL is preferably within a range from 2:8 to 8:2, and even more preferably from 3:7 to 7:3.

Furthermore, as the organic solvent, mixed solvents containing at least one of PGMEA and EL, together with γ-butyrolactone, are also preferred. In such cases, the weight ratio of the former and latter components in the mixed solvent is preferably within a range from 70:30 to 95:5.

There are no particular restrictions on the quantity used of the organic solvent, although the quantity should provide a concentration that enables favorable application of the solution to a support such as a substrate or the like, and should be set in accordance with the required coating film thickness, and is typically set so that the solid fraction concentration within the resist composition falls within a range from 2 to 20% by weight, and even more preferably from 5 to 15% by weight.

<Method for Forming Resist Pattern>

A method for forming a resist pattern that uses a positive resist composition according to the present invention can be conducted, for example, in the manner described below.

Namely, a positive resist composition described above is first applied to a support such as a silicon wafer using a spinner or the like, a prebake is then conducted under temperature conditions of 80 to 150° C., for a period of 40 to 120 seconds, and preferably for 60 to 90 seconds, and following selective exposure (irradiation) of the thus obtained film with an ArF exposure apparatus or the like, by irradiating ArF excimer laser light through a desired mask pattern, PEB (post exposure baking) is conducted under temperature conditions of 80 to 150° C., for a period of 40 to 120 seconds, and preferably for 60 to 90 seconds. Subsequently, developing is conducted using an alkali developing solution such as a 0.1 to 10% by weight aqueous solution of tetramethylammonium hydroxide. In this manner, a resist pattern that is faithful to the mask pattern can be obtained.

An organic or inorganic anti-reflective film may also be provided between the support (substrate) and the applied layer of the resist composition.

As the support, conventional materials can be used without any particular restrictions, and suitable examples include substrates for electronic componentry, as well as substrates on which a predetermined wiring pattern has already been formed.

Specific examples of suitable substrates include silicon wafers, metal-based substrates such as copper, chrome, iron, and aluminum, as well as glass substrates.

Suitable materials for the wiring pattern include copper, solder, chrome, aluminum, nickel, and gold.

There are no particular restrictions on the wavelength used for the exposure (irradiation), and an ArF excimer laser, KrF excimer laser, $F_2$ excimer laser, or other radiation such as EUV (extreme ultraviolet), VUV (vacuum ultraviolet), EB (electron beam), X-ray or soft X-ray radiation can be used. A positive resist composition according to the present invention is particularly effective for use with an ArF excimer laser.

The conditions employed during the resist pattern formation, such as the revolution rate during resist application, the prebake temperature, the exposure conditions, the post exposure baking conditions, and the alkali developing conditions may all be set to conventional levels. Specifically, the revolution rate is typically approximately 2,000 rpm, and specifically within a range from 1,200 to 3,500 rpm, and the prebake temperature is typically within a range from 70 to 130° C., and such conditions form a resist film with a thickness of 80 to 250 μm. Exposure is typically conducted through a mask. The mask used for selective exposure can employ a conventional mask such as a typical binary mask or phase shift mask. The post exposure baking temperature is typically within a range from 90 to 140° C., and the alkali developing conditions typically involve developing for 15 to 90 seconds at 23° C., using a 1 to 5% by weight TMAH (tetramethylammonium hydroxide) developing solution, followed by rinsing with water.

As described above, a resist pattern obtained using a positive resist composition that includes either the polymer compound (AA) or (A) according to the present invention exhibits excellent resolution. Moreover, even if an acid generator that generates a comparatively weak acid is used, a favorable resist pattern can still be resolved, meaning the present invention offers the advantage of allowing a broader selection of potential acid generators.

It is surmised that these effects are the result of the fact that in the polymer compound (A) or (AA) (the compound (AA) also includes the structural unit (a1)), the aforementioned structural unit (a1) contains a plurality of (meth)acrylate units, exhibits favorable acid dissociability, and includes the group A that is readily dissociable. In other words, because the structural unit (a1) includes a plurality of (meth)acrylate units, the alkali solubility improves following dissociation of the group A, which functions as an acid dissociable, dissolution inhibiting group, thereby enhancing the contrast in alkali solubility between the exposed portions and unexposed portions of the resist, and improving the resolution. Furthermore, as shown above in the formula (51), it is thought that because the structural unit includes a structure in which the methyl groups of each of the ester side chain portions of the (meth)acrylate units are bonded to the group A via an oxygen atom, the group A dissociates readily even under the action of comparatively weak acids such as the acid generated from an onium salt containing a camphorsulfonate ion as the anion, meaning a favorable resist pattern can be resolved even in those cases where an acid generator is used for which the strength of the acid generated is comparatively weak.

In addition, in the present invention, it is expected that this improvement in the alkali solubility within the exposed portions will also provide a reduction in the occurrence of developing defects and a reduction in line edge roughness.

Furthermore, as favorable resolution performance can be achieved even with onium salts containing a camphorsulfonate ion as the anion, it is expected that favorable resolution performance will also be obtainable using other non-ionic acid generators that generate comparatively stronger acids, such as diazomethane-based acid generators.

As a result, it is expected that a positive resist composition of the present invention will also be able to be used as a material for immersion lithography. Immersion lithography is a method wherein the space between the lens and the resist layer on the wafer, which has conventionally been filled with air or an inert gas such as nitrogen during exposure, is instead filled with a solvent that has a larger refractive index than air, such as pure water or a fluorine-based inert solvent, and it is claimed that even with the same exposure wavelength light source, this method enables higher resolutions to be achieved with no reduction in the depth of focus, which are effects that usually require the use of a shorter wavelength light source or a high NA lens. In this type of immersion lithography, if an ionic acid generator such as an onium salt is used as the acid generator, then a problem arises in that the acid generator within the resist film is eluted into, and contaminates the water during immersion. Accordingly, it is expected that the positive resist composition of the present invention, which is able to employ non-ionic acid generators, will be useful as a material for immersion lithography.

EXAMPLES

Synthesis of Halogenated Ether Compounds

Synthesis Example 1

Synthesis of 1,2-bis(chloromethoxy)ethane (19)

Paraformaldehyde was added to 1,2-ethanediol, a 2.0 to 3,0-fold equivalence of hydrogen chloride gas relative to the 1,2-ethanediol was blown into the reaction system, and the reaction was continued at 50° C. for 12 hours. Following completion of the reaction, the reaction product was subjected to distillation under reduced pressure, yielding 1,2-bis(chloromethoxy)ethane (19).

Synthesis Example 2

Synthesis of 1,3-bis(chloromethoxy)propane (20)

Paraformaldehyde was added to 1,3-propanediol, a 2.0 to 3,0-fold equivalence of hydrogen chloride gas relative to the 1,3-propanediol was blown into the reaction system, and the reaction was continued at 50° C. for 12 hours. Following completion of the reaction, the reaction product was subjected to distillation under reduced pressure, yielding 1,3-bis(chloromethoxy)propane (20).

Synthesis Example 3

Synthesis of 1,4-bis(chloromethoxymethyl)cyclohexane (21)

Paraformaldehyde was added to 1,4-cyclohexanedimethanol, a 2.0 to 3.0-fold equivalence of hydrogen chloride gas relative to the 1,4-cyclohexanedimethanol was blown into the reaction system, and the reaction was continued at 50° C. for 12 hours. Following completion of the reaction, the reaction product was subjected to distillation under reduced pressure, yielding 1,4-bis(chloromethoxymethyl)cyclohexane (21).

Chemical formulas for the halogenated ether compounds (19) through (21) synthesized in the manner described above are shown below.

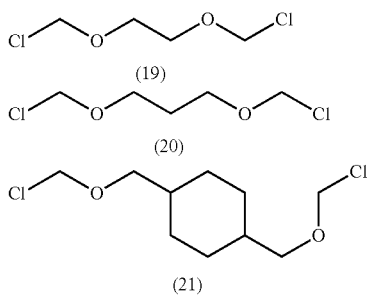

[Incorporation of Halogenated Ether Compound into Alkali-Soluble Resin]

Using the procedures outlined in the resin synthesis examples 1 through 4 described below, the halogenated ether compounds represented by the chemical formulas (19) through (21) shown above were incorporated into a commercially available resin 1 or resin 2, which are represented by the chemical formulas (22) and (23) shown below and are synthesized by an addition polymerization or radical polymerization, thereby yielding resins 3 through 6, which represent polymer compounds of the present invention.

The resin 1 through resin 6 are represented by the chemical formulas (22) through (27) respectively, shown below. The results of chemical analyses of these resins (including the weight average molecular weight, the polydispersity, and the incorporation rate of acid dissociable, dissolution inhibiting groups) are shown in Table 1.

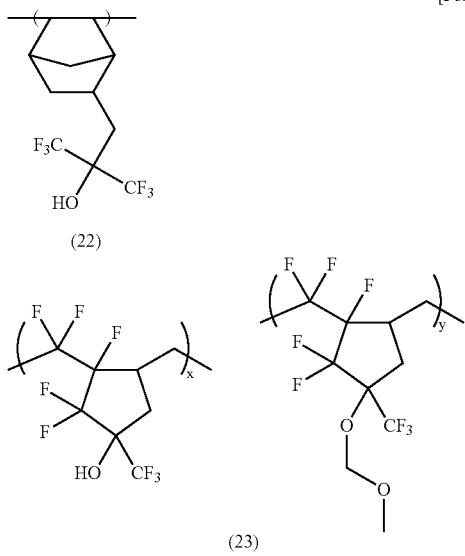

Resin Synthesis Example 1

27.4 g of the resin 1 (22) was dissolved in 300 mL of tetrahydrofuran, and 2.2 g of sodium hydride was added to the solution. The solution was stirred at room temperature until a uniform solution was obtained, and 7.9 g of 1,2-bis(chloromethoxy)ethane (19) was then added dropwise to the solution. The resulting mixture was subsequently stirred for 12 hours at room temperature, and the precipitated salt was separated by filtration. The thus obtained filtrate was then added dropwise to 1 L of water. The precipitated resin was collected by filtration, dried under reduced pressure, dissolved in tetrahydrofuran, and then added dropwise to 1 L of n-heptane. The precipitated resin was once again collected by filtration and dried under reduced pressure, yielding a white resin powder. The yield was 26.5 g. This resin is termed resin 3 (24).

Resin Synthesis Example 2

27.4 g of the resin 1 (22) was dissolved in 300 mL of tetrahydrofuran, and 2.2 g of sodium hydride was added to the solution. The solution was stirred at room temperature until a uniform solution was obtained, and 8.7 g of 1,3-bis(chloromethoxy)propane (20) was then added dropwise to the solution. The resulting mixture was subsequently stirred for 12 hours at room temperature, and the precipitated salt was separated by filtration. The thus obtained filtrate was then added dropwise to 1 L of water. The precipitated resin was collected by filtration, dried under reduced pressure, dissolved in tetrahydrofuran, and then added dropwise to 1 L of n-heptane. The precipitated resin was once again collected by filtration and dried under reduced pressure, yielding a white resin powder. The yield was 25.5 g. This resin is termed resin 4 (25).

Resin Synthesis Example 3

27.4 g of the resin 1 (22) was dissolved in 300 mL of tetrahydrofuran, and 2.2 g of sodium hydride was added to the solution. The solution was stirred at room temperature until a uniform solution was obtained, and 12.0 g of 1,4-bis(chloromethoxymethyl)cyclohexane (21) was then added dropwise to the solution. The resulting mixture was subsequently stirred for 12 hours at room temperature, and the precipitated salt was separated by filtration. The thus obtained filtrate was then added dropwise to 1 L of water. The precipitated resin was collected by filtration, dried under reduced pressure, dissolved in tetrahydrofuran, and then added dropwise to 1 L of n-heptane. The precipitated resin was once again collected by filtration and dried under reduced pressure, yielding a white resin powder. The yield was 26.5 g. This resin is termed resin 5 (26).

Resin Synthesis Example 4

10.0 g of the resin 2 (23) was dissolved in 100 mL of tetrahydrofuran, and 2.4 g of sodium hydride was added to the solution. The solution was stirred at room temperature until a uniform solution was obtained, and 0.9 g of 1,2-bis(chloromethoxy)ethane (19) was then added dropwise to the solution. The resulting mixture was subsequently stirred for 12 hours at room temperature, and the precipitated salt was separated by filtration. The thus obtained filtrate was then added dropwise to 1 L of water. The precipitated resin was collected by filtration, dried under reduced pressure, dissolved in tetrahydrofuran, and then added dropwise to 1 L of n-heptane. The precipitated resin was once again collected by filtration and dried under reduced pressure, yielding a white resin powder. The yield was 8.9 g. This resin is termed resin 6 (27).

[Formula 40]
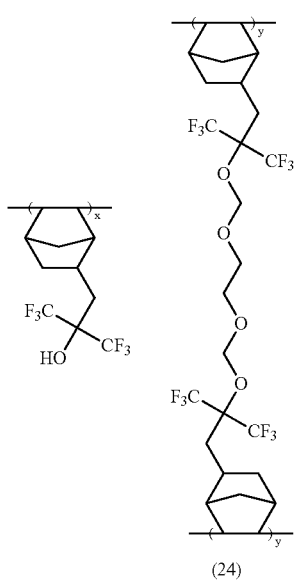
(24)
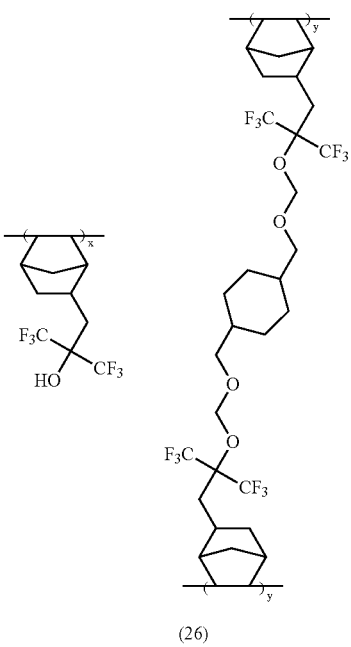
(26)
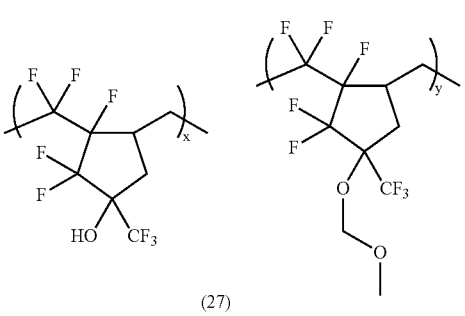
(27)
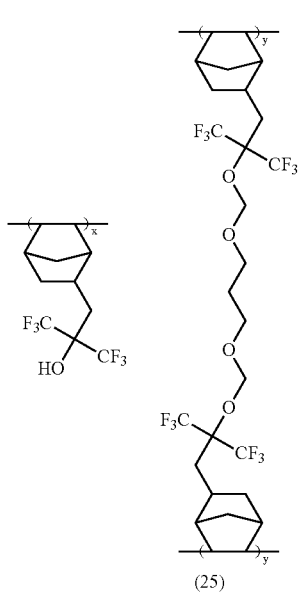
(25)
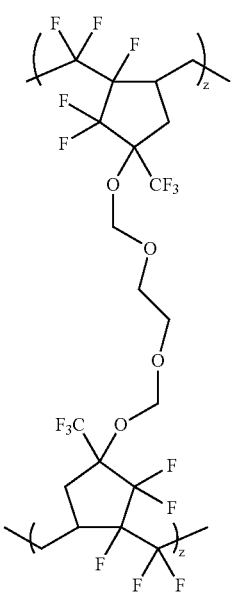

TABLE 1

|  | Molecular weight (Mw) | Polydispersity (Mw/Mn) | Composition ratio (x/y or x/y/z) |
|---|---|---|---|
| Resin 1 | 7,500 | 1.74 | — |
| Resin 2 | 25,200 | 2.20 | 0.81/0.19 |
| Resin 3 | 96,900 | — | 0.63/0.37 |
| Resin 4 | 76,100 | — | 0.62/0.38 |
| Resin 5 | 111,200 | — | 0.65/0.35 |
| Resin 6 | 48,600 | — | 0.7/0.19/0.11 |

Example 1

Confirmation of Exposure Resolution of Positive Photoresist

An organic anti-reflective film composition AR-19 (a product name, manufactured by Shipley Co., Ltd.) was applied to the surface of a silicon wafer using a spinner, and was baked and dried at 215° C. for 90 seconds on top of a hotplate, thereby forming an organic anti-reflective film with a thickness of 82 nm. The positive photoresist composition described below was applied to the above organic anti-reflective film using a spinner, and was then prebaked and dried at 110° C. for 90 seconds on a hotplate, thus forming a resist layer with a film thickness of 200 nm. Subsequently, this layer was selectively irradiated with an ArF excimer laser (193 nm) through a mask pattern (a halftone mask with a transmission rate of 6%), using an ArF exposure apparatus NSR-S302 (manufactured by Nikon Corporation, NA (numerical aperture)=0.60, ⅔ annular illumination). The irradiated resist was subjected to PEB treatment at 90° C. for 60 seconds, was subsequently subjected to puddle development for 30 seconds at 23° C. in a 2.38% by weight aqueous solution of tetramethylammonium hydroxide, and was then washed for 20 seconds with water and dried, thereby completing formation of a resist pattern.

As a result, a 110 nm line and space pattern was formed, and the pattern shape exhibited favorable rectangular formability. The exposure dose was 11 mJ/cm$^2$.

Positive Photoresist Composition:

The positive photoresist composition was prepared using the resin 6, together with the acid generator and quencher shown below.

| | |
|---|---|
| Resin 6 (27) | 100 parts by weight |
| Acid generator: triphenylsulfonium perfluorobutanesulfonate (hereafter abbreviated as TPS-PFBS) | 4.0 parts by weight |
| Quencher (nitrogen-containing organic compound): triisopropanolamine | 0.4 parts by weight |
| Organic solvent: propylene glycol monomethyl ether acetate (hereafter abbreviated as PGMEA) | 1250 parts by weight |

Example 2

Measurement of Dissolution Rate within Alkali Developing Solution

Using the resin 6 (27), the change in dissolution rate of the positive photoresist upon changing the exposure dose of a F$_2$ excimer laser was measured using a dissolution rate analyzer RDA-808RB (manufactured by Lithotech Japan Corp.), and the dissolution contrast (tan θ) was determined. The obtained tan θ value is shown in Table 2. The positive photoresist composition was prepared using the resin 6, together with the acid generator and quencher shown below.

| | |
|---|---|
| Resin 6 (27) | 100 parts by weight |
| Acid generator: TPS-PFBS | 5.0 parts by weight |
| Quencher: triisopropanolamine | 0.1 parts by weight |
| Organic solvent: PGMEA | 1250 parts by weight |

Comparative Example 1

Confirmation of Exposure Resolution of Positive Photoresist

Using the resin 2 (23), the resolution of a positive photoresist was confirmed for ArF exposure.

The resolution, pattern shape and exposure dose are shown in Table 2. The positive photoresist composition was prepared using the resin 2, together with the acid generator and quencher shown below.

| | |
|---|---|
| Resin 2 (23) | 100 parts by weight |
| Acid generator: TPS-PFBS | 4.0 parts by weight |
| Quencher: triisopropanolamine | 0.4 parts by weight |
| Solvent: methyl amyl ketone (MAK) | 1250 parts by weight |

Comparative Example 2

Measurement of Dissolution Rate within Alkali Developing Solution

Using the resin 2 (23), the change in dissolution rate of the positive photoresist upon changing the exposure dose of a F$_2$ excimer laser was measured using a dissolution rate analyzer RDA-808RB (manufactured by Lithotech Japan Corp.), and the dissolution contrast (tan θ) was determined. The obtained tan θ value is shown in Table 2. The positive photoresist composition was prepared using the resin 2, together with the acid generator and quencher shown below.

| | |
|---|---|
| Resin 2 (23) | 100 parts by weight |
| Acid generator: TPS-PFBS | 5.0 parts by weight |
| Quencher: triisopropanolamine | 0.1 parts by weight |
| Solvent: PGMEA | 1250 parts by weight |

TABLE 2

| | Resin | ArF exposure Resolution (nm) | ArF exposure Sensitivity (mJ/cm²) | Pattern shape | Dissolution contrast (tan θ) |
|---|---|---|---|---|---|
| Example 1 | Resin 6 | 110 | 11 | Rectangular | — |
| Example 2 | Resin 6 | — | — | — | 11 |
| Comparative example 1 | Resin 2 | 110 | 11 | Rounded | — |
| Comparative example 2 | Resin 2 | — | — | — | 3.8 |

As shown in Table 2, the resin 6 (the example 2) that represents one example of a polymer compound of the present invention exhibited a higher dissolution contrast (tan θ) than that of the resin 2 of the comparative example 2, and as a result, even though the resolution and sensitivity for ArF exposure were similar to those for the resin 2 of the comparative example 2, it was very evident that the pattern shape for the resin 6 was far superior (rectangular).

Monomer Synthesis Example 1

17.2 g of methacrylic acid was dissolved in 400 mL of tetrahydrofuran, and 21.2 g of triethylamine was added to the solution. Following stirring at room temperature, a solution containing 15.9 g of the halogenated ether compound represented by the above chemical formula (19) (1,2-bis(chloromethoxy)ethane) dissolved in 100 mL of tetrahydrofuran was added dropwise to the solution. The resulting mixture was subsequently stirred for 12 hours at room temperature, and the precipitated salt was separated by filtration. The solvent was removed from the thus obtained filtrate, the resulting product was dissolved in 200 mL of ethyl acetate and washed with pure water (3 repetitions of 100 mL), and the solvent was then removed. A colorless oily product was obtained. This compound is deemed the monomer 1.

The results of measuring the infrared absorption spectrum and proton nuclear magnetic resonance spectrum ($^1$H-NMR) of the monomer 1 are shown below. Furthermore, the structure of the monomer 1 is represented by a formula (m1) shown below.

IR (cm$^{-1}$): 2962 (C=H stretch), 1725 (C=O stretch), 1638 (C=C stretch) $^1$H-NMR (CDCl$_3$, internal standard: tetramethylsilane) ppm: 1.97 (s, 6H), 3.85 (s, 4H), 5.40 (s, 4H), 5.64 (s, 2H), 6.18 (s, 2H)

[Formula 41]

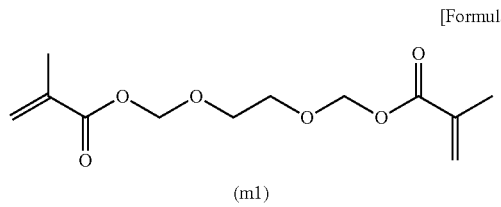

(m1)

Monomer Synthesis Example 2

17.2 g of methacrylic acid was dissolved in 400 mL of tetrahydrofuran, and 21.2 g of triethylamine was added to the solution. Following stirring at room temperature, a solution containing 17.3 g of the halogenated ether compound represented by the above chemical formula (20) (1,3-bis(chloromethoxy)propane) dissolved in 100 mL of tetrahydrofuran was added dropwise to the solution. The resulting mixture was subsequently stirred for 12 hours at room temperature, and the precipitated salt was separated by filtration. The solvent was removed by vaporization from the thus obtained filtrate, the resulting product was dissolved in 200 mL of ethyl acetate and washed with pure water (3 repetitions of 100 mL), and the solvent was then removed by vaporization. A colorless oily product was obtained. This compound is deemed the monomer 2.

The results of measuring the infrared absorption spectrum and proton nuclear magnetic resonance spectrum ($^1$H-NMR) of the monomer 2 are shown below. Furthermore, the structure of the monomer 2 is represented by a formula (m2) shown below.

IR (cm$^{-1}$): 2961 (C=H stretch), 1726 (C=O stretch), 1638 (C=C stretch) $^1$H-NMR (CDCl$_3$, internal standard: tetramethylsilane) ppm: 1.88 to 1.95 (m, 8H), 3.74 to 3.77 (m, 4H), 5.35 (s, 4H), 5.62 (s, 2H), 6.18 (s, 2H)

[Formula 42]

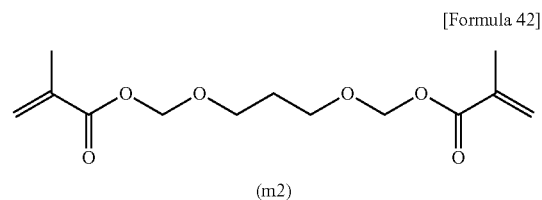

(m2)

Monomer Synthesis Example 3

17.2 g of methacrylic acid was dissolved in 400 mL of tetrahydrofuran, and 21.2 g of triethylamine was added to the solution. Following stirring at room temperature, a solution containing 24.1 g of the halogenated ether compound represented by the above chemical formula (21) (1,4-bis(chloromethoxymethyl)cyclohexane) dissolved in 100 mL of tetrahydrofuran was added dropwise to the solution. The resulting mixture was subsequently stirred for 12 hours at room temperature, and the precipitated salt was separated by filtration. The solvent was removed by vaporization from the thus obtained filtrate, the resulting product was dissolved in 200 mL of ethyl acetate and washed with pure water (3 repetitions of 100 mL), and the solvent was then removed by vaporization. A colorless oily product was obtained. This compound is deemed the monomer 3.

The results of measuring the infrared absorption spectrum and proton nuclear magnetic resonance spectrum ($^1$H-NMR) of the monomer 3 are shown below. Furthermore, the structure of the monomer 3 is represented by a formula (m3) shown below.

IR (cm$^{-1}$): 2924, 2859 (C—H stretch), 1725 (C=O stretch), 1638 (C=C stretch) $^1$H-NMR (CDCl$_3$, internal standard: tetramethylsilane) ppm: 0.95 to 1.96 (m, 16H), 3.45 to 3.55 (m, 4H), 5.34 (s, 4H), 5.6 (s, 2H), 6.15 (s, 2H)

[Formula 43]

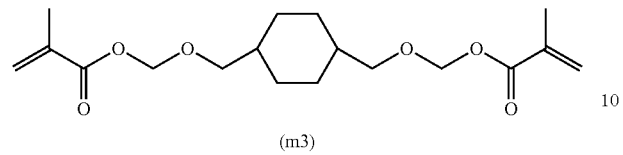

(m3)

Resin Synthesis Example 5

0.6 g of the monomer 1 (m1), 5.0 g of 2-methyl-2-adamantyl methacrylate (represented by a formula (m4) shown below), and 4.5 g of γ-butyrolactone methacrylate (represented by a formula (m5) shown below) were dissolved in 100 mL of tetrahydrofuran, and 0.41 g of azobisisobutyronitrile was added. The reaction solution was refluxed for 6 hours and then added dropwise to 1 L of n-heptane. The precipitated resin was collected by filtration and dried under reduced pressure, yielding a white resin powder (represented by a formula (p1) shown below). This resin is termed resin 7.

The weight average molecular weight (Mw) of the resin 7 was 11,800, and the polydispersity (Mw/Mn) was 2.0. Furthermore, measurement of the carbon-13 nuclear magnetic resonance spectrum ($^{13}$C-NMR) revealed a composition ratio (molar ratio) of x:y:z=29.5:66.1:4.4.

[Formula 44]

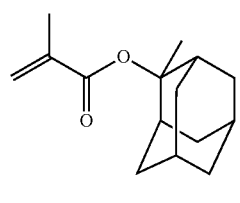

(m4)

[Formula 45]

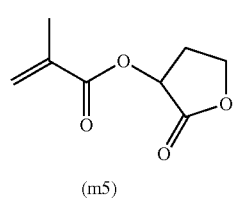

(m5)

[Formula 46]

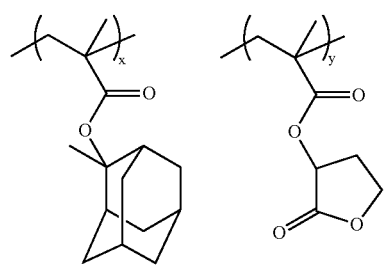

(p1)

-continued

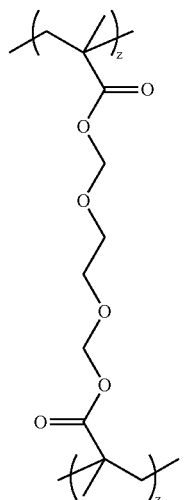

Resin Synthesis Example 6

1.4 g of the monomer 1 (m1), 2.5 g of 2-methyl-2-adamantyl methacrylate (represented by the formula (m4) shown above), and 1.8 g of γ-butyrolactone methacrylate (represented by the formula (m5) shown above) were dissolved in 200 mL of tetrahydrofuran, and 0.22 g of azobisisobutyronitrile was added. The reaction solution was refluxed for 6 hours and then added dropwise to 2 L of n-heptane. The precipitated resin was collected by filtration and dried under reduced pressure, yielding a white resin powder (of the formula (p1) shown above). This resin is termed resin 8.

The weight average molecular weight (Mw) of the resin 8 was 5,400, and the polydispersity (Mw/Mn) was 2.0. Furthermore, measurement of the carbon-13 nuclear magnetic resonance spectrum ($^{13}$C-NMR) revealed a composition ratio (molar ratio) of x:y:z=22.7:49.2:28.1.

Resin Synthesis Example 7

0.5 g of the monomer 1 (m1), 2.1 g of γ-butyrolactone methacrylate (represented by the formula (m5) shown above), and 2.5 g of 2-adamantoxy methacrylate (represented by a formula (m6) shown below) were dissolved in 200 mL of tetrahydrofuran, and 0.20 g of azobisisobutyronitrile was added. The reaction solution was refluxed for 6 hours and then added dropwise to 2 L of n-heptane. The precipitated resin was collected by filtration and dried under reduced pressure, yielding a white resin powder (represented by a formula (p2) shown below). This resin is termed resin 9.

The weight average molecular weight (Mw) of the resin 9 was 14,400. Furthermore, measurement of the carbon-13 nuclear magnetic resonance spectrum ($^{13}$C-NMR) revealed a composition ratio (molar ratio) of x:y:z=31.7:50.4:17.9.

[Formula 47]

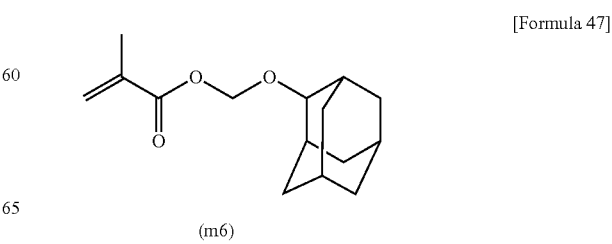

(m6)

-continued

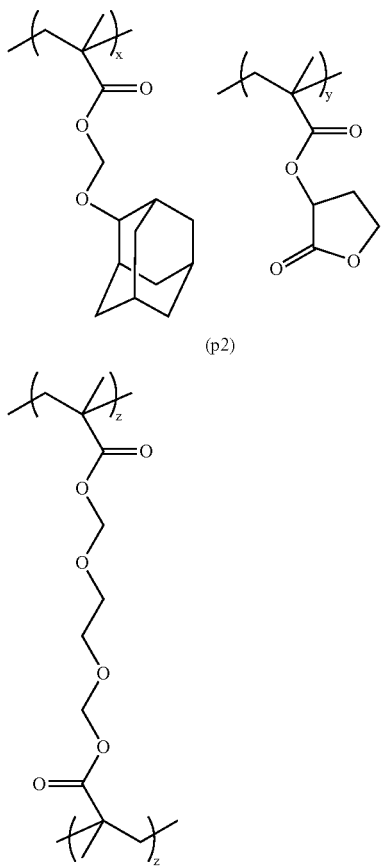

(p2)

Resin Synthesis Example 8

1.3 g of the monomer 1 (m1), 1.7 g of γ-butyrolactone methacrylate (represented by the formula (m5) shown above), and 2.5 g of 2-adamantoxy methacrylate (represented by the formula (m6) shown above) were dissolved in 200 mL of tetrahydrofuran, and 0.20 g of azobisisobutyronitrile was added. The reaction solution was refluxed for 6 hours and then added dropwise to 2 L of n-heptane. The precipitated resin was collected by filtration and dried under reduced pressure, yielding a white resin powder (of the formula (p2) shown above). This resin is termed resin 10.

The weight average molecular weight (Mw) of the resin 10 was 7,200, and the polydispersity (Mw/Mn) was 2.0. Furthermore, measurement of the carbon-13 nuclear magnetic resonance spectrum ($^{13}$C-NMR) revealed a composition ratio (molar ratio) of x:y:z=22.9:34.5:42.6.

Comparative Resin Synthesis Example 1

10.6 g of 2-methyl-2-adamantyl methacrylate (represented by the formula (m4) shown above) and 15.0 g of γ-butyrolactone methacrylate (represented by the formula (m5) shown above) were dissolved in 230 mL of tetrahydrofuran, and 0.74 g of azobisisobutyronitrile was added. The reaction solution was refluxed for 12 hours and then added dropwise to 2 L of n-heptane. The precipitated resin was collected by filtration and dried under reduced pressure, yielding a white resin powder (represented by a formula (p3) shown below). This resin is termed comparative resin 1.

The weight average molecular weight (Mw) of the comparative resin 1 was 8,780. Furthermore, measurement of the carbon-13 nuclear magnetic resonance spectrum ($^{13}$C-NMR) revealed a composition ratio (molar ratio) of x:y=64:36.

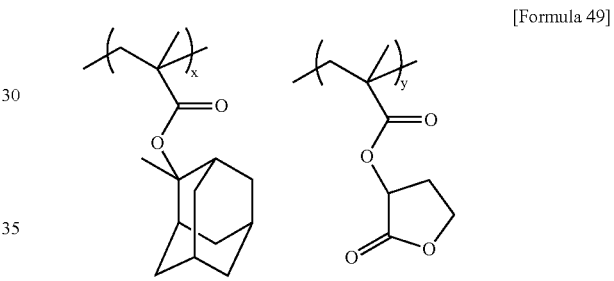

(p3)

The results of the above synthesis examples are summarized below in Table 3.

TABLE 3

|  | m4 (mol %) | m6 (mol %) | m5 (mol %) | m1 (mol %) | m7 (mol %) | Weight average molecular weight (Mw) |
| --- | --- | --- | --- | --- | --- | --- |
| Resin synthesis example 5 | 29.5 | — | 66.1 | 4.4 | — | 11,800 |
| Resin synthesis example 6 | 22.7 | — | 49.2 | 28.1 | — | 5,400 |
| Resin synthesis example 7 | — | 31.7 | 50.4 | 17.9 | — | 14,400 |
| Resin synthesis example 8 | — | 22.9 | 34.5 | 42.6 | — | 7,200 |
| Comparative resin synthesis example 1 | 64 | — | 36 | — | — | 8,780 |

Example 3

An organic anti-reflective film composition ARC-29 (manufactured by Brewer Science Ltd.) was applied to the surface of a silicon wafer using a spinner, and the composition was then baked and dried on a hotplate at 205° C. for 60 seconds, thereby forming an organic anti-reflective film with a thickness of 77 nm. Each of the positive photoresist compositions with the compositions shown below in Table 4 was then applied to one of the above organic anti-reflective films using a spinner, and was then prebaked and dried at 120° C. for 90 seconds on a hotplate, thus forming a resist layer with a film thickness of 250 nm. Subsequently, this layer was selectively irradiated with an ArF excimer laser (193 nm) through a mask pattern, using an ArF exposure apparatus NSR-S302 (manufactured by Nikon Corporation, NA (numerical aperture)=0.60, ⅔ annular illumination). The irradiated resist was subjected to PEB treatment at 120° C. for 60 seconds, was subsequently subjected to puddle development for 60 seconds at 23° C. in a 2.38% by weight aqueous solution of tetramethylammonium hydroxide, and was then washed for 60 seconds with water, and dried, thereby completing formation of a resist pattern. The results are shown in Table 5.

TABLE 4

| | (A) Resin | (B) Acid generator | (D) Nitrogen-containing organic compound | Organic solvent | Other |
|---|---|---|---|---|---|
| Example 1 | Resin 7 (100 parts by weight) | TPS-PFBS (3 parts by weight) | Triethanolamine (0.35 parts by weight) | PGMEA (1230 parts by weight) | γ-butyrolactone (20 parts by weight) |
| Example 2 | Resin 9 (100 parts by weight) | Compound (b-1) (4.7 parts by weight) | Triethanolamine (0.35 parts by weight) | PGMEA (1230 parts by weight) | γ-butyrolactone (20 parts by weight) |
| Comparative example 1 | Comparative resin 1 (100 parts by weight) | Compound (b-1) (4.7 parts by weight) | Triethanolamine (0.35 parts by weight) | PGMEA (1230 parts by weight) | γ-butyrolactone (20 parts by weight) |

TPS-PFBS: triphenylsulfonium nonafluorobutanesulfonate

TABLE 5

| | Resolution (L/S) | Sensitivity (mJ/cm²) |
|---|---|---|
| Example 1 | 110 nm | 32 |
| Example 2 | 130 nm | 45 |
| Comparative example 1 | not resolvable | — |

<Sensitivity>

The exposure dose required to form a 130 nm line and space pattern in a 1:1 ratio was measured as the sensitivity (Eop) in units of mJ/cm² (the quantity of energy).

<Resolution>

The resolution limit at the above Eop value was determined from a SEM photograph.

As described above, positive photoresist compositions containing the resin 7 or 9, which represent examples of polymer compounds of the present invention, were able to resolve high resolution resist patterns regardless of the type of acid generator that was used.

In contrast, in the positive photoresist composition of the comparative example 1, which used the compound represented by the above formula (b-1) as the acid generator, which generates a weaker acid than that generated by TPS-PFBS, the resist pattern was unable to be resolved.

INDUSTRIAL APPLICABILITY

A described above, when used within a chemically amplified positive resist system, a polymer compound according to the present invention produces a significant change in alkali solubility from the state prior to exposure to that following exposure, and is therefore useful for forming fine patterns with a high level of resolution, and is ideal for forming fine patterns using exposure by KrF, ArF or F₂ excimer lasers.

The invention claimed is:

1. A compound represented by a general formula (41) shown below:

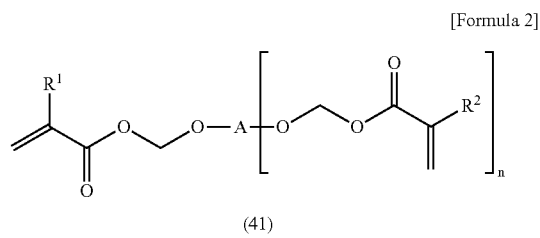

[Formula 2]

(41)

[wherein, $R^1$ and $R^2$ each represent, independently, a hydrogen atom or a methyl group; n represents an integer from 1 to 4; and A represents a straight-chain saturated hydrocarbon group of 2 to 4 carbon atoms, or a hydrocarbon group containing a cyclic group of 4 to 15 carbon atoms with a valency of (n+1)].

2. A compound according to claim 1, represented by either general formula (42) or general formula (43) shown below:

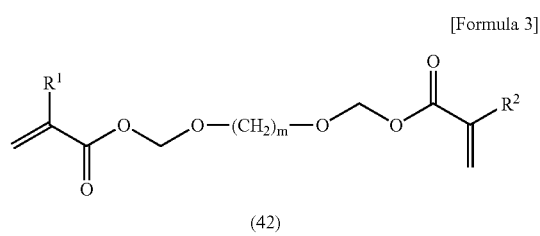

[Formula 3]

(42)

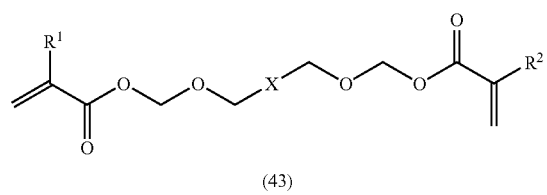

(43)

[wherein, $R^1$ and $R^2$ each represent, independently, a hydrogen atom or a methyl group; m represents an integer of 2 or 3; and X represents a cyclic saturated hydrocarbon group of 4 to 15 carbon atoms].

3. A compound according to claim 1, represented by one of general formulas (44), (45) and (46) shown below:

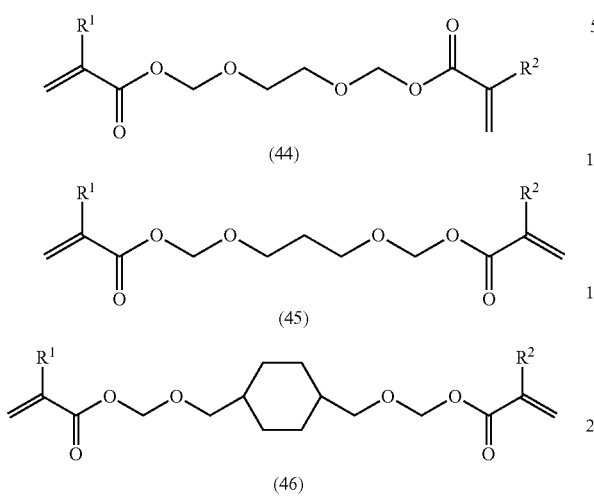

[wherein, $R^1$ and $R^2$ each represent, independently, a hydrogen atom or a methyl group].

4. A polymer compound comprising a structural unit (a1) represented by a general formula (51) shown below:

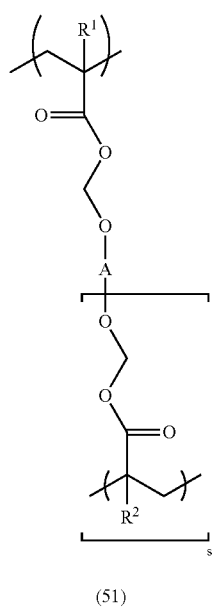

[wherein, $R^1$ and $R^2$ each represent independently, a hydrogen atom or a methyl group; s represents an integer from 1 to 4; and A represents a straight-chain saturated hydrocarbon group of 2 to 4 carbon atoms, or a hydrocarbon group containing a cyclic group of 4 to 15 carbon atoms with a valency of (s+1)].

5. A polymer compound according to claim 4, further comprising a structural unit (a2) derived from a mono (α-lower alkyl) acrylate ester that contains an acid dissociable, dissolution inhibiting group.

6. A polymer compound according to claim 5, wherein said structural unit (a2) comprises a structural unit represented by a general formula (61) or a general formula (64) shown below:

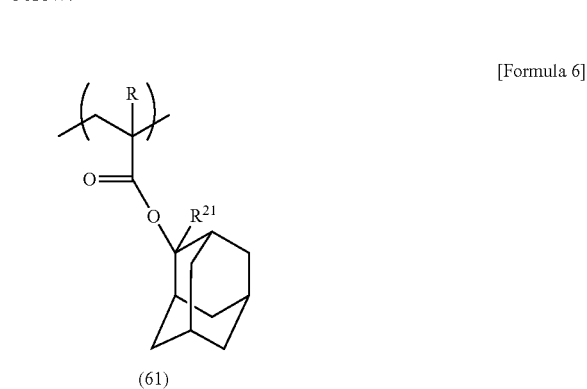

[wherein, R represents a hydrogen atom or a lower alkyl group, and $R^{21}$ represents a lower alkyl group];

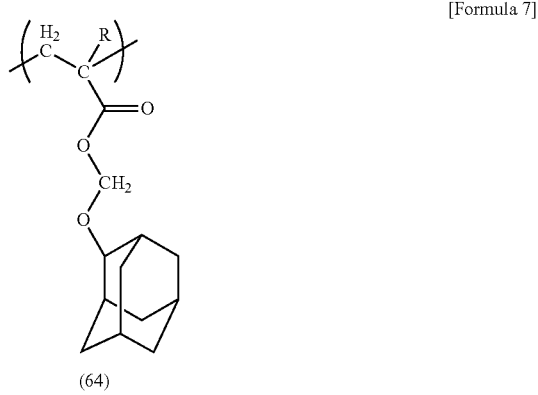

[wherein, R represents a hydrogen atom or a lower alkyl group].

7. A polymer compound according to any one of claims 4, 5 and 6, further comprising a structural unit (a3) derived from a mono (α-lower alkyl) acrylate ester that contains a lactone-containing monocyclic or polycyclie group.

8. A polymer compound according to claim 7, wherein said structural unit (a3) comprises a structural unit represented by a general formula (31) shown below:

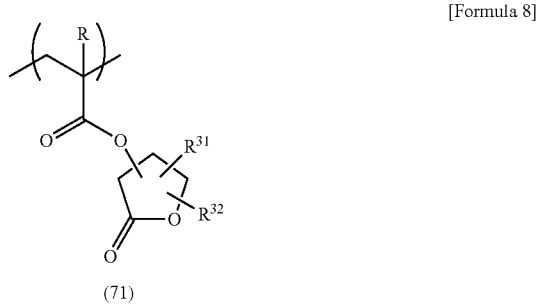

[wherein, R represents a hydrogen atom or a lower alkyl group; and $R^{31}$ and $R^{32}$ each represent, independently, a hydrogen atom or a lower alkyl group].

9. A polymer compound according to claim 4, wherein said polymer compound is a copolymer comprising structural units represented by a general formula (A1) shown below, a copolymer comprising structural units represented by a general formula (A2) shown below, a copolymer comprising structural units represented by a general formula (A3) shown below, or a copolymer comprising structural units represented by a general formula (A4) shown below:

[Formula 9]

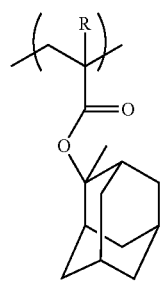 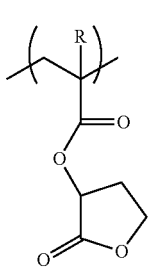 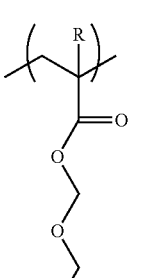

(A1)

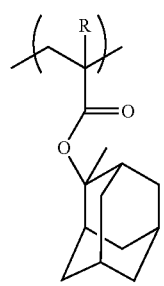 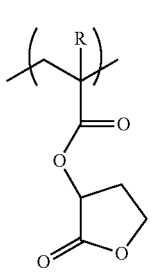

(A2)

[Formula 10]

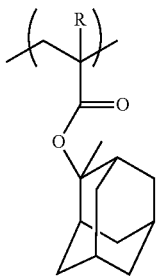 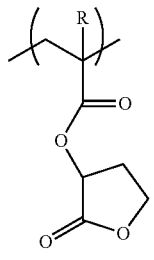 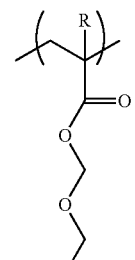

(A3)

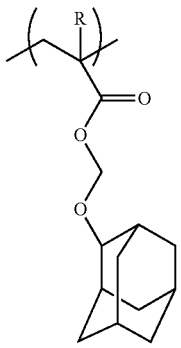 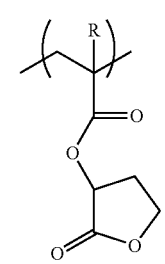 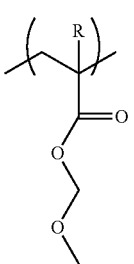

(A4)

[wherein, R represents a hydrogen atom or a methyl group].

10. A polymer compound according to claim 4, with a weight average molecular weight within a range from 2,000 to 50,000.

11. A positive resist composition, comprising a polymer compound (A) according to claim 4, and an acid generator component (B) that generates acid on exposure.

12. A positive resist composition according to claim 11, wherein said acid generator component (B) that generates acid on exposure is an onium salt that contains a camphorsulfonate ion as an anion.

13. A positive resist composition according to claim 11, further comprising a nitrogen-containing organic compound.

14. A method for forming a resist pattern, comprising the steps of applying a positive resist composition according to claim 11 to a substrate, conducting a prebake, performing selective exposure, conducting PEB (post exposure baking), and performing alkali developing to form a resist pattern.

* * * * *